(12) United States Patent
Taniguchi et al.

(10) Patent No.: US 7,666,206 B2
(45) Date of Patent: Feb. 23, 2010

(54) SURGICAL INSTRUMENT

(75) Inventors: Kazunori Taniguchi, Tokyo (JP); Toru Nagase, Tokyo (JP)

(73) Assignee: Olympus Corporation (JP)

( * ) Notice: Subject to any disclaimer, the term of this patent is extended or adjusted under 35 U.S.C. 154(b) by 566 days.

(21) Appl. No.: 10/630,509

(22) Filed: Jul. 30, 2003

(65) Prior Publication Data

US 2004/0073210 A1 Apr. 15, 2004

(30) Foreign Application Priority Data

Jul. 30, 2002 (JP) .............................. 2002-221709

(51) Int. Cl.
*A61B 17/00* (2006.01)
(52) U.S. Cl. ..................................... 606/206
(58) Field of Classification Search ................... 606/70, 606/174, 201–208, 45–51; 128/751; 600/201–205
See application file for complete search history.

(56) References Cited

U.S. PATENT DOCUMENTS

| 5,275,608 | A | * | 1/1994 | Forman et al. ............... 606/170 |
| 5,383,888 | A | * | 1/1995 | Zvenyatsky et al. ......... 606/206 |
| 5,417,203 | A |   | 5/1995 | Tovey et al. .................... 128/4 |
| 5,549,637 | A |   | 8/1996 | Crainich ...................... 606/207 |
| 5,827,323 | A | * | 10/1998 | Klieman et al. ............. 606/205 |
| 6,936,061 | B2 | * | 8/2005 | Sasaki ......................... 606/205 |
| 7,090,689 | B2 | * | 8/2006 | Nagase et al. ............... 606/205 |
| 2002/0055758 | A1 | * | 5/2002 | Sasaki ......................... 606/205 |
| 2004/0098040 | A1 | * | 5/2004 | Taniguchi et al. ........... 606/205 |

\* cited by examiner

*Primary Examiner*—Anhtuan T Nguyen
*Assistant Examiner*—Tuan V Nguyen
(74) *Attorney, Agent, or Firm*—Ostrolenk Faber LLP

(57) ABSTRACT

A surgical instrument has an insertion section, an operation section disposed in a proximal end of the insertion section, and a treatment section disposed in a distal end of the insertion section. First and second driving rods are disposed in the insertion section. The operation section is opened/closed and rotated to transmit an opening/closing force to the first driving rod, and a rotating force to the second driving rod. The treatment section comprises a pair of jaws. The treatment section is connected to the distal end portions of the first and second driving rods disposed in the insertion section to rotate and open/close the pair of jaws with respect to the insertion section.

15 Claims, 30 Drawing Sheets

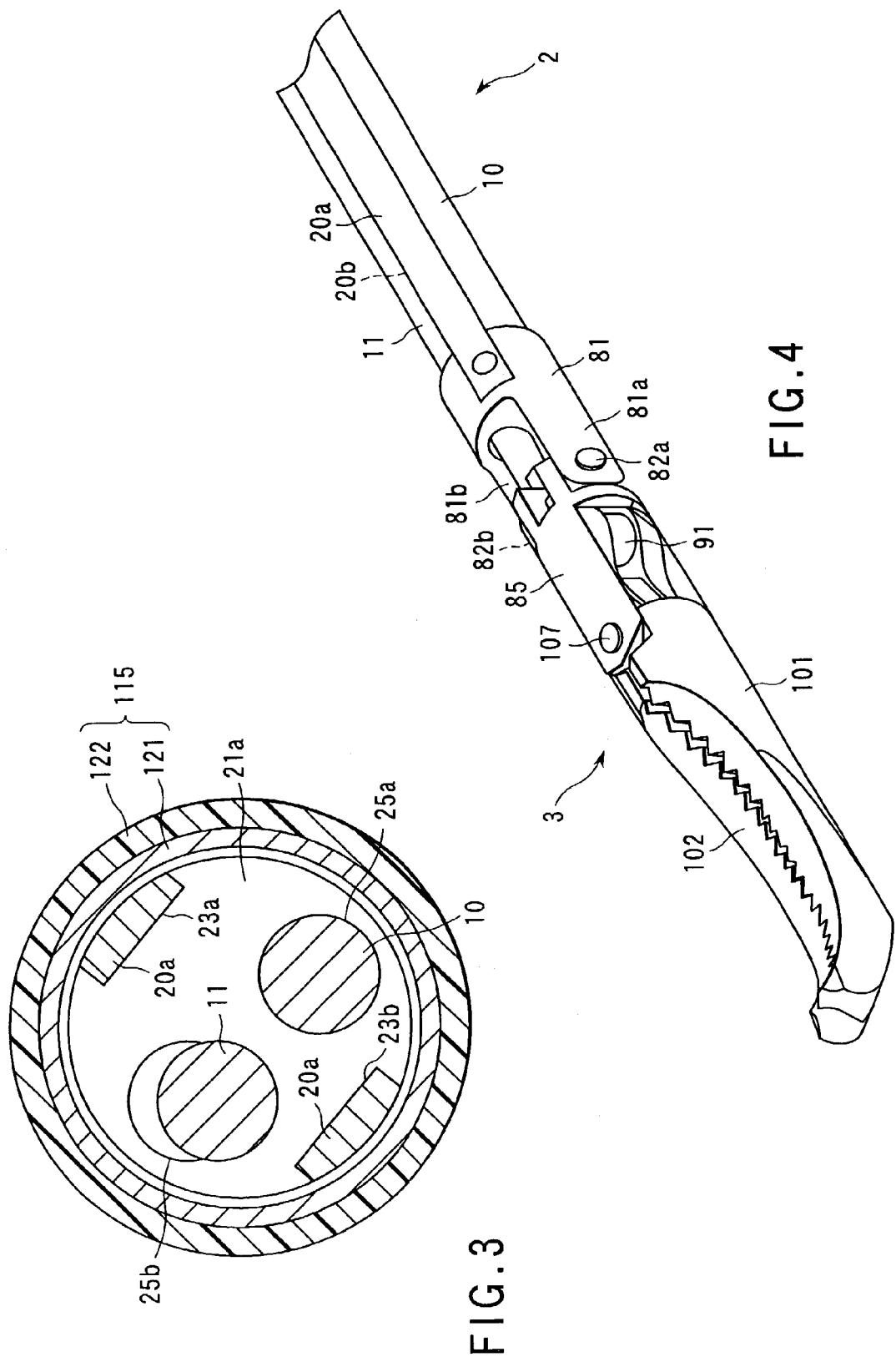

SURGICAL INSTRUMENT

CROSS-REFERENCE TO RELATED APPLICATIONS

This application is based upon and claims the benefit of priority from the prior Japanese Patent Application No. 2002-221709, filed Jul. 30, 2002, the entire contents of which are incorporated herein by reference.

BACKGROUND OF THE INVENTION

1. Field of the Invention

The present invention relates to a surgical instrument which operates a treatment section disposed in a distal end of an insertion section by an operation section disposed in a proximal end of the insertion section.

2. Description of the Related Art

For example, U.S. Pat. Nos. 5,383,888, 5,417,203, 5,549,637 etc., disclose surgical instruments. In these surgical instruments, distal ends of treatment sections can be rotated.

In the surgical instruments disclosed in U.S. Pat. Nos. 5,383,888 and 5,417,203, the distal ends of the treatment sections can be rotated, and tip-tools disposed in the distal ends of the treatment sections can be opened/closed. In the surgical instrument described in U.S. Pat. No. 5,383,888, an opening/closing operation is carried out utilizing the tension of a flexible cable connected to the tip-tool. In the tip-tool of the surgical instrument described in U.S. Pat. No. 5,417,203, a joint portion to realize rotation of the tip-tool is made of a shape memory alloy.

The surgical instrument disclosed in U.S. Pat. No. 5,549,637 is a surgical stapler. In the distal end of the treatment section of the stapler, three joints are disposed to rotate the distal end. Each joint has a rotational angle of 60°. A pair of bands is connected to the distal end of the treatment section of the stapler. The three joints in the distal end of the treatment section are sequentially rotated by tensing or slackening the bands. Accordingly, the distal end of the treatment section of the stapler can be changed in direction by 180° (6°×3) with respect to an insertion direction of the stapler.

BRIEF SUMMARY OF THE INVENTION

According to an aspect of the present invention, a surgical instrument includes an insertion section, a pair of jaws, a support, a sliding member, a connecting rod, a rotation mechanism and an operation section disposed in the proximal end portion of the insertion section. The insertion section has first and second driving rods which are disposed side by side. The pair of jaws is disposed in the distal end portion of the insertion section. The support pivotally supports at least one of the pair of jaws to be relatively opened/closed. The sliding member is supported by at least one of the pair of jaws being pivotally supported by the support. The sliding member slides in an axial direction of the support with respect to the support to relatively open/close at least one of the pair of jaws being pivotally supported by the support. The sliding member being pivotally supported on the distal end portion of the connecting rod to open/close the pair of jaws, and the distal end portion of the first driving rod being pivotally supported on the proximal end portion of the connecting rod. The rotation mechanism rotatably supports the support at the distal end portion of the insertion section, and pivotally supports the support at the distal end portion of the second driving rod in a state of being offset with respect to a center axis of the support. The operation section pivotally supports the proximal end portions of the first and second driving rods, when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support at the distal end portion of the insertion section, thereby rotating the pair of jaws with respect to the insertion section relatively.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a sectional view along the line A-A of FIG. 2, showing a regulation member of the insertion section in the surgical instrument of the first embodiment.

FIG. 4 is a perspective view of a state seen from above where the treatment section is set straight with respect to the insertion section while a sheath is removed from the insertion section in the surgical instrument of the first embodiment.

DETAILED DESCRIPTION OF THE INVENTION

Description will be made of the preferred embodiments of the present invention with reference to the accompanying drawings. First, a first embodiment will be described with reference to FIGS. 1 to 29.

Figure 1:
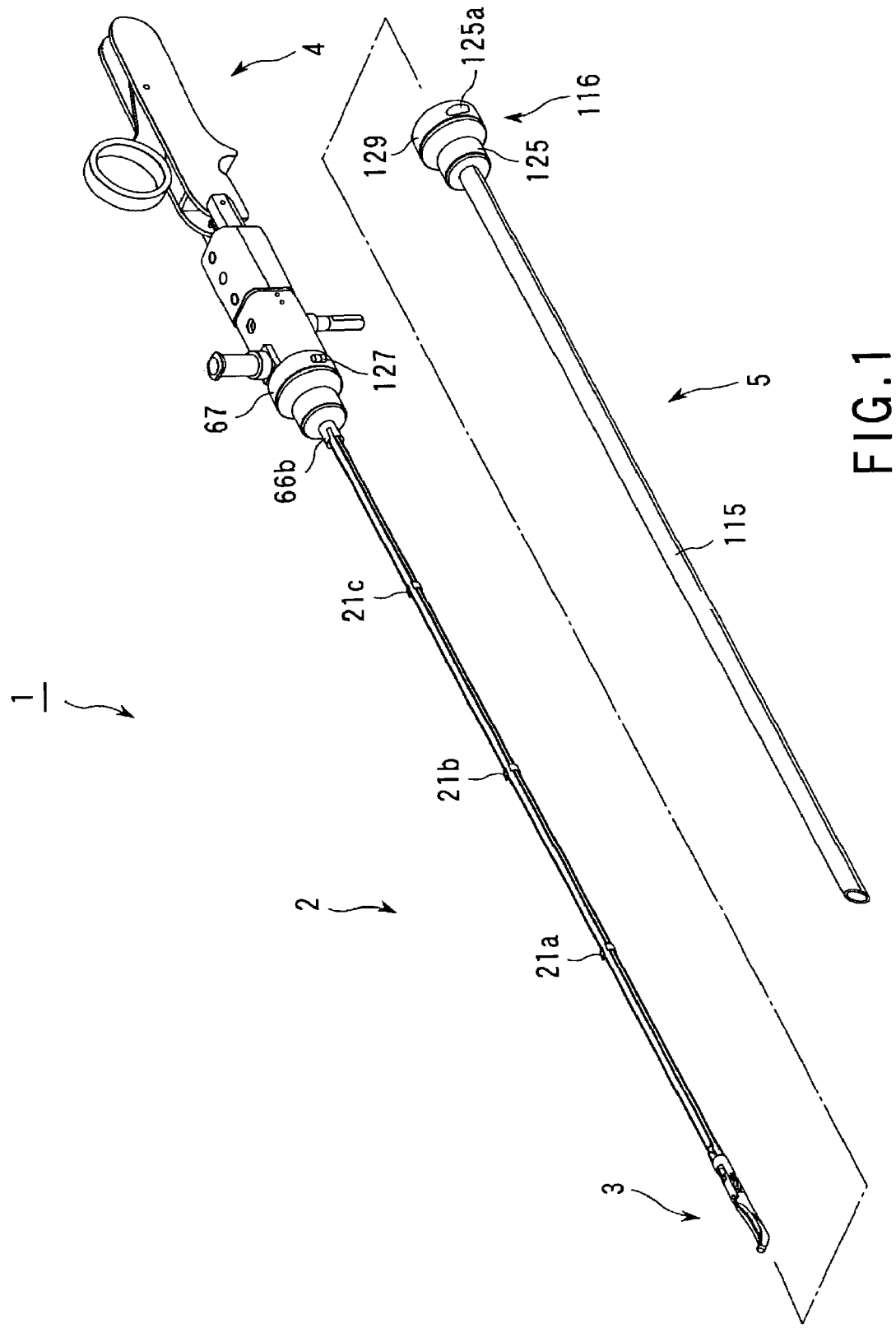
FIG. 1 is a perspective view showing a surgical instrument according to a first embodiment.
Figure 2:
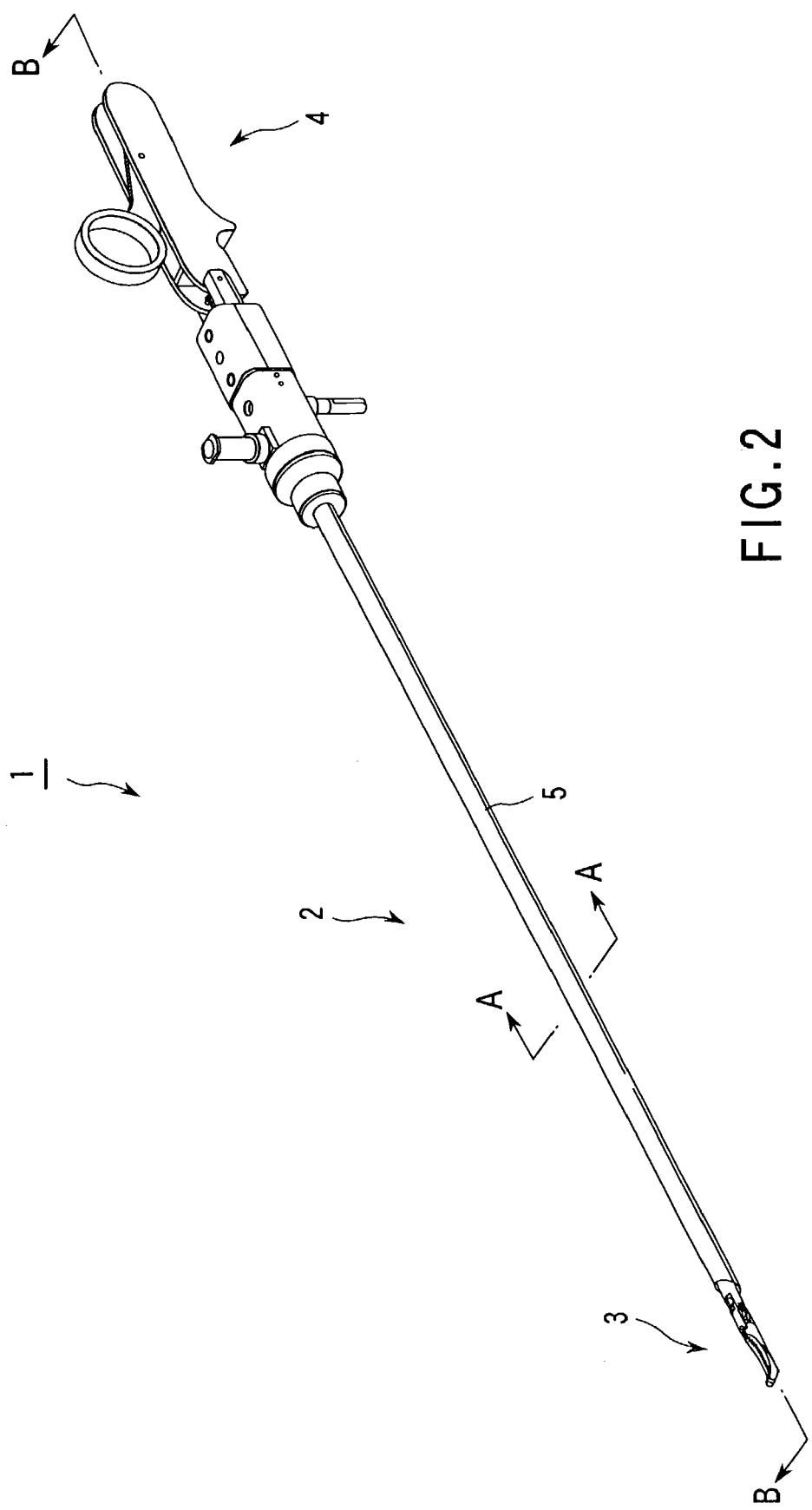
FIG. 2 is a perspective view of a state seen from above where an operation section and a treatment section are set straight with respect to an insertion section, showing an entire constitution of the surgical instrument of the first embodiment.

As shown in FIG. 1, a surgical instrument 1 of the embodiment has a thin and long insertion section 2, a treatment section 3 disposed in a distal end of the insertion section 2, and an operation section 4 disposed in a proximal end of the insertion section 2. When the operation section 4 is operated, the treatment section 3 is operated by remote control. As shown in FIG. 2, during use of the surgical instrument 1, an outer periphery of the insertion section 2 is covered with a thin and long sheath 5. The sheath 5 is a type of an elongate member.

As shown in FIGS. 3 to 15, especially FIGS. 3 and 4, a thin and long first driving rod (treatment section opening/closing driving rod) 10 and a thin and long second driving rod (treatment section rotation driving rod) 11 are arranged in parallel or roughly in parallel with each other in the insertion section 2. Each of the first and second driving rods 10, 11 is, e.g., circular in section, and formed as a small-diameter rod with an outer diameter of several millimeters. Each of the first and second driving rods 10, 11 are mainly made of a conductive and rigid metal material, e.g., a stainless material.

Figure 12:
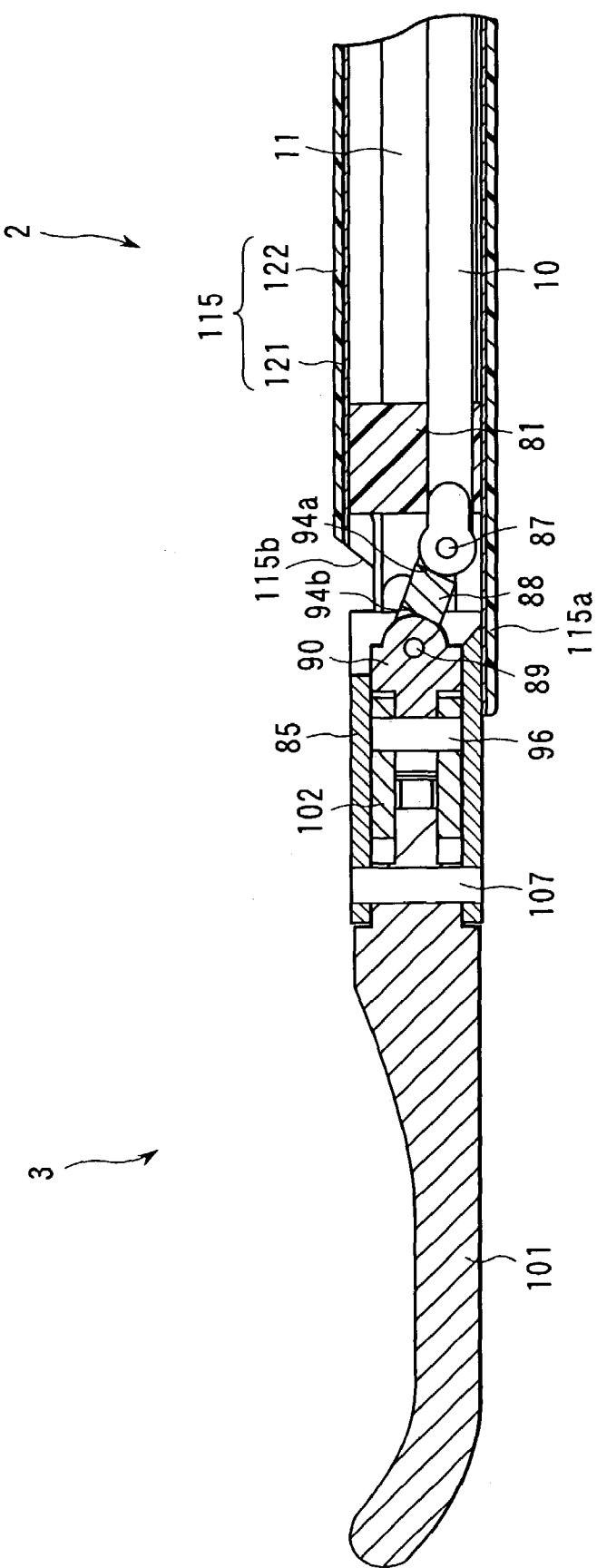
FIG. 12 is a sectional view along the line B-B of FIG. 2 showing a state where the treatment section is set straight with respect to the insertion section in the surgical instrument of the first embodiment.

As shown in FIGS. 12 to 15, especially FIG. 12, a distal end surface of the first driving rod 10 is formed in a circular-arc shape. That is, a distal end of the first driving rod 10 has a shape similar to an outer peripheral surface of a thin disk which has an axis in a direction orthogonal to an axial direction of the first driving rod 10. As shown in FIGS. 16 to 19, especially FIG. 16, a proximal end of the first driving rod 10 is formed similarly to the distal end of the same. Axes of the outer periphery of the thin disk on the distal and proximal ends of the first driving rod 10 are parallel to each other.

Figure 8:
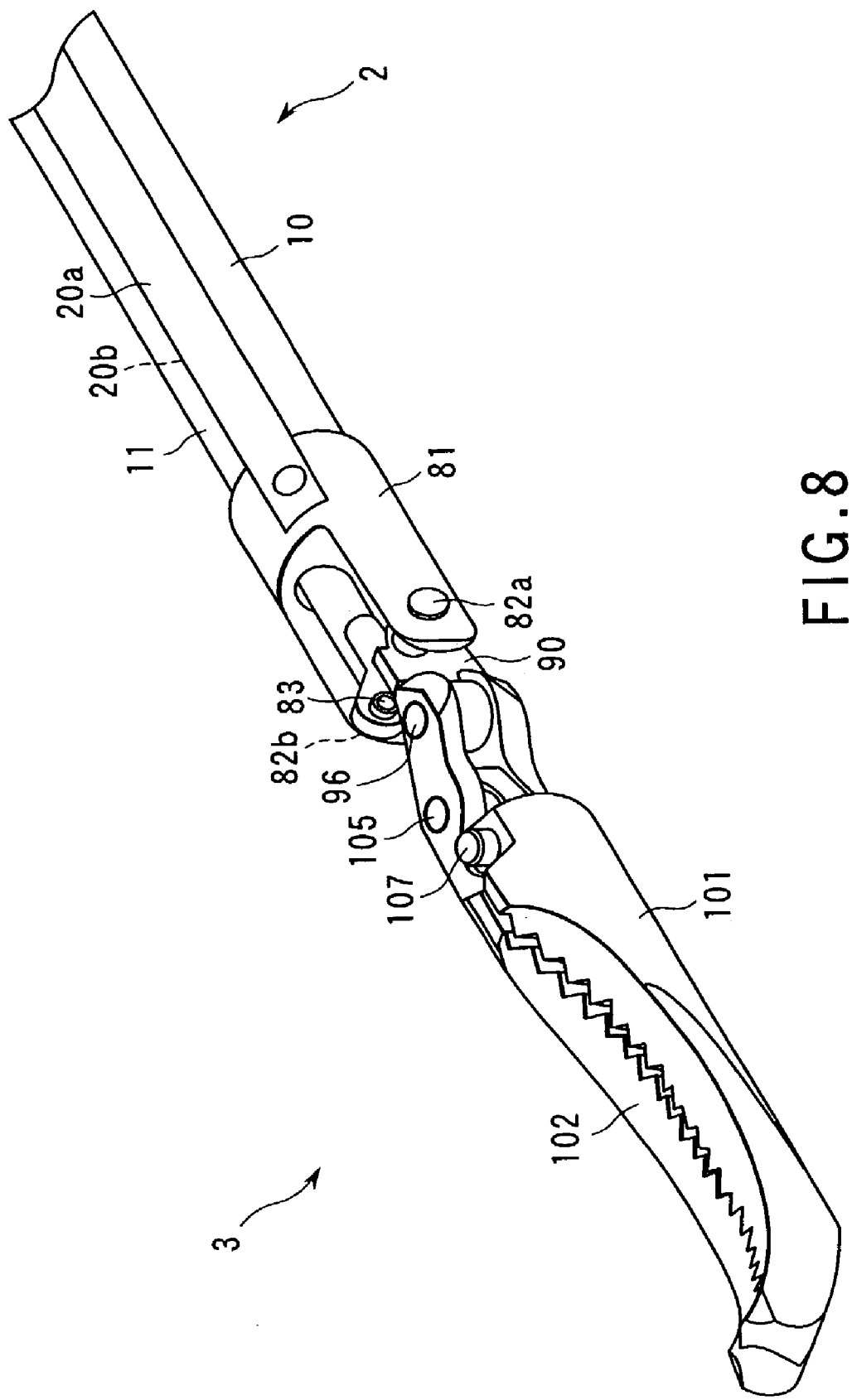
FIG. 8 is a perspective view of a state seen from above where the treatment section is set straight with respect to the insertion section while the sheath and a rotary cover are removed from the insertion section and the treatment section in the surgical instrument of the first embodiment.
Figure 9:
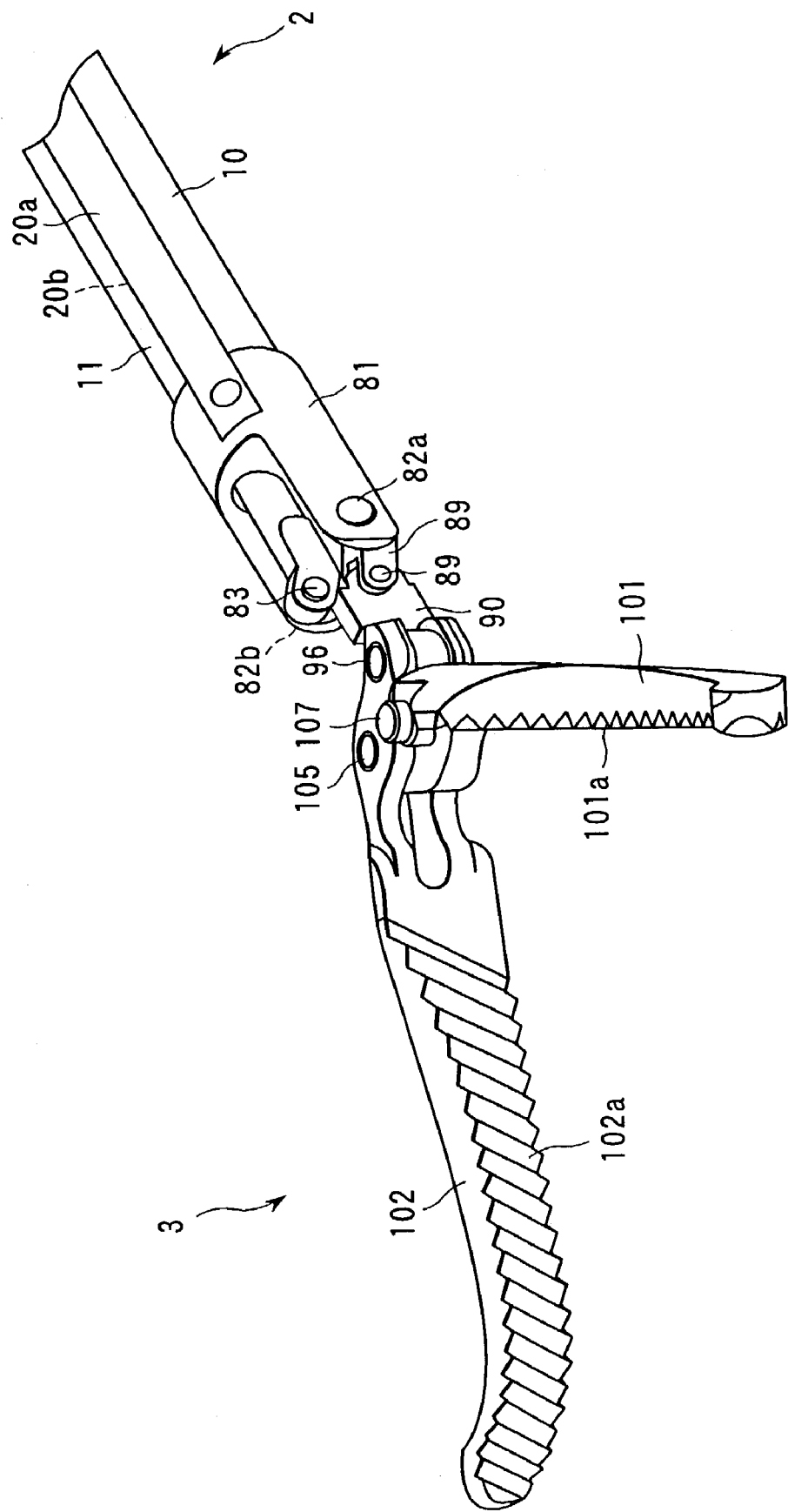
FIG. 9 is a perspective view of a state seen from above where the jaw of the treatment section is opened while the sheath and the rotary cover are removed from the insertion section and the treatment section in the surgical instrument of the first embodiment.
Figure 16:
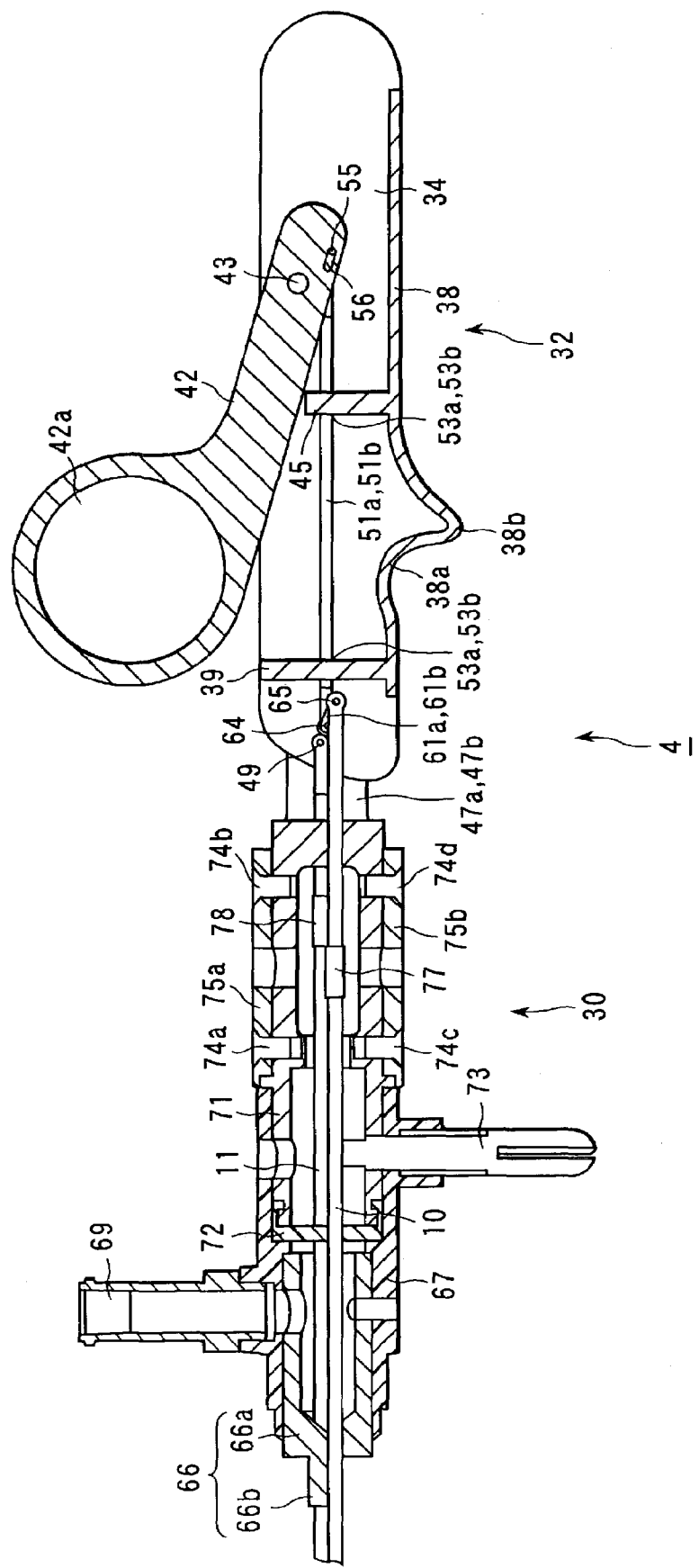
FIG. 16 is a sectional view along the line B-B of FIG. 2 showing a state where an opening/closing handle of the operation section is closed with respect to a rotary handle in the surgical instrument of the first embodiment.
Figure 18:
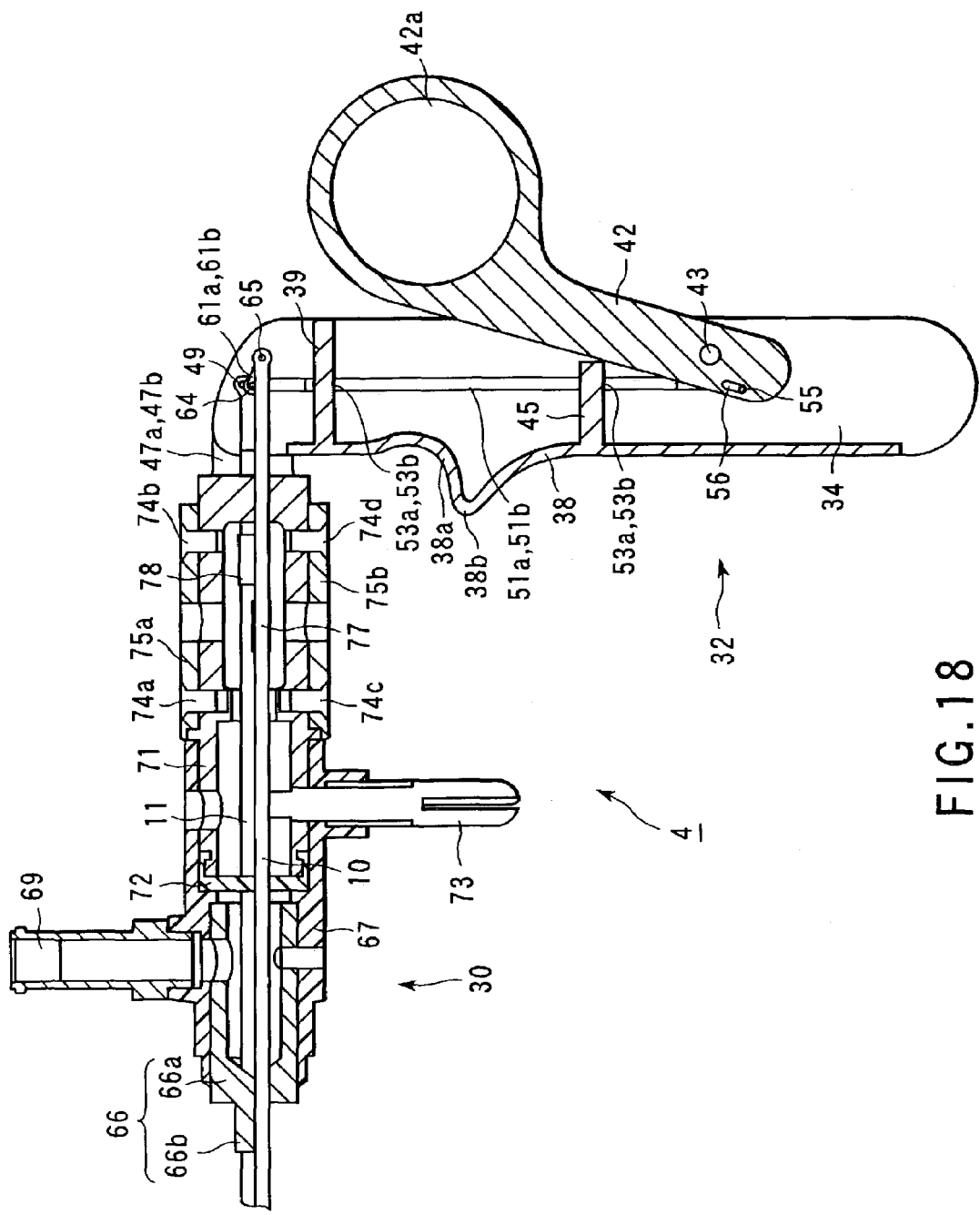
FIG. 18 is a sectional view along the line B-B of FIG. 2 showing a state where the rotary handle of the operation section is lowered with respect to an operation section main body in the surgical instrument of the first embodiment.

As shown in FIGS. 8 and 9, a distal end of the second driving rod 11 is bent obliquely upward toward the front in the axial direction of the second driving rod 11. As shown in FIGS. 16 and 18, a proximal end of the second driving rod 11 is bent obliquely upward toward the rear side in the axial direction of the second driving rod 11. An up-and-down direction means a direction in which a later-described rotary handle 32 is rotated with respect to an operation section main body 30. A downward direction means a direction in which the rotary handle 32 and the operation section main body 30 can be rotated from a state of being on the same axis (see FIGS. 16 and 18). A left-and-right direction means a direction orthogonal to the up-and-down direction.

As shown in FIGS. 4 to 11, especially FIG. 4, for example, a pair of frames 20a, 20b are disposed in the insertion section 2 to be extended in the axial directions of the first and second driving rods 10, 11. These frames 20a, 20b are made of rigid metals, e.g., stainless materials. As shown in FIG. 1, in the insertion section 2, three regulation members 21a to 21c are sequentially arranged at equal intervals in an axial direction of the insertion section to regulate movements of the first and second driving rods 10, 11 with respect to the insertion section 2.

The regulation members 21a to 21c have shapes roughly similar to one another. As shown in FIG. 3, the regulation member 21a is formed on a roughly circular surface. On an outer peripheral surface of the regulation member 21a, a pair of recesses 23a, 23b are formed in opposite positions with respect to a center axis of the regulation member 21a. The frames 20a, 20b are fitted to be fixed in the recesses 23a, 23b. Outer peripheral surfaces of the frames 20a, 20b are formed in shapes along the outer peripheral surface of the regulation member 21a when they are fitted in the recesses 23a, 23b. As the frames 20a, 20b are fixed in the recesses 23a, 23b of the regulation member 21a, the insertion section 2 becomes circular in a position of the regulation member 21a.

First and second through-holes 25a, 25b are formed in the regulation member 21a. When the regulation member 21a is viewed from the treatment section 3 side, the first through-hole 25a is positioned lopsidedly downward from the center axis of the insertion section 2, and lopsidedly to the right of the center axis of the insertion section 2. An inner diameter of the first through-hole 25a is slightly larger than an outer diameter of the first driving rod 10. The first driving rod 10 is arranged to penetrate the first through-hole 25a of the regulation member 21a. Thus, the first driving rod 10 can move back and forth in the axial direction of the insertion section 2.

The second through-hole 25b has a roughly elliptical shape which has a long axis in the up-and-down direction. When the regulation member 21a is viewed from the treatment section 3 side, the second through-hole 25b is positioned in the vicinity of the center axis of the insertion section 2 in the up-and-down direction, and lopsidedly to the left of the center axis of the insertion section 2. A left-and-right direction (short axis direction) width of the second through-hole 25b is slightly larger than an outer diameter of the second driving rod 11. A longitudinal direction (long axis direction) width of the second through-hole 25b is larger by about 1.5 times than the outer diameter of the second driving rod 11. Accordingly, the second driving rod 11 can move back and forth in the axial direction of the insertion section 2 through the regulation members 21a to 21c, and can also move within a predetermined range in the up-and-down direction. When the surgical instrument 1 is assembled, since there is a space in the up-and-down direction, even if the second driving rod 11 is inserted through the through-hole 25b, the distal and proximal ends bent in the axial direction of the second driving rod 11 can be easily inserted through the second through-hole 25b.

Next, description will be made of the operation section 4 disposed in the proximal end of the insertion section 2 of the surgical instrument 1 with reference to FIGS. 16 to 21.

Figure 19:
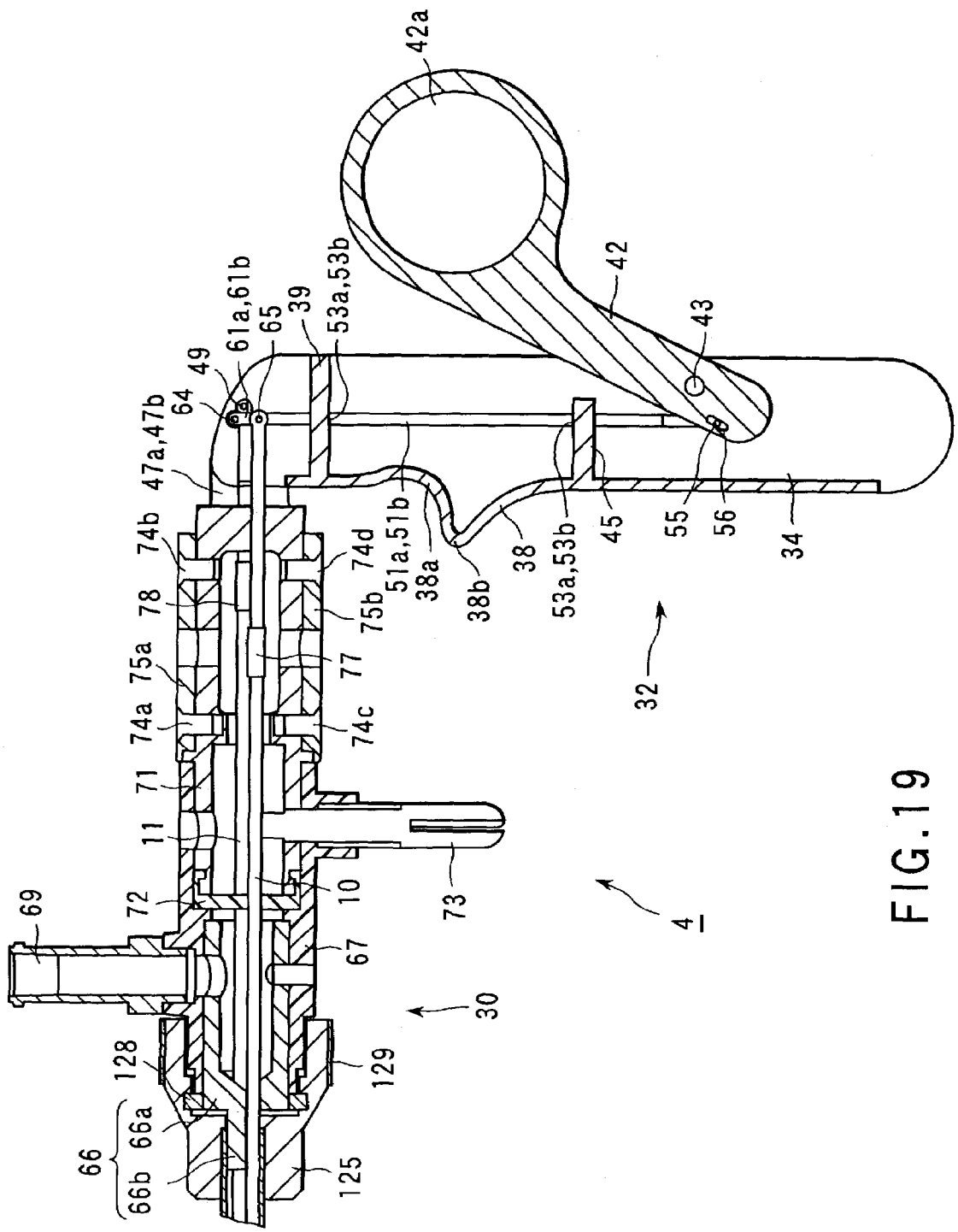
FIG. 19 is a sectional view along the line B-B of FIG. 2 showing a state where the rotary handle of the operation section is lowered with respect to the operation section main body and the opening/closing handle is opened with respect to the rotary handle in the surgical instrument of the first embodiment.
Figure 20:
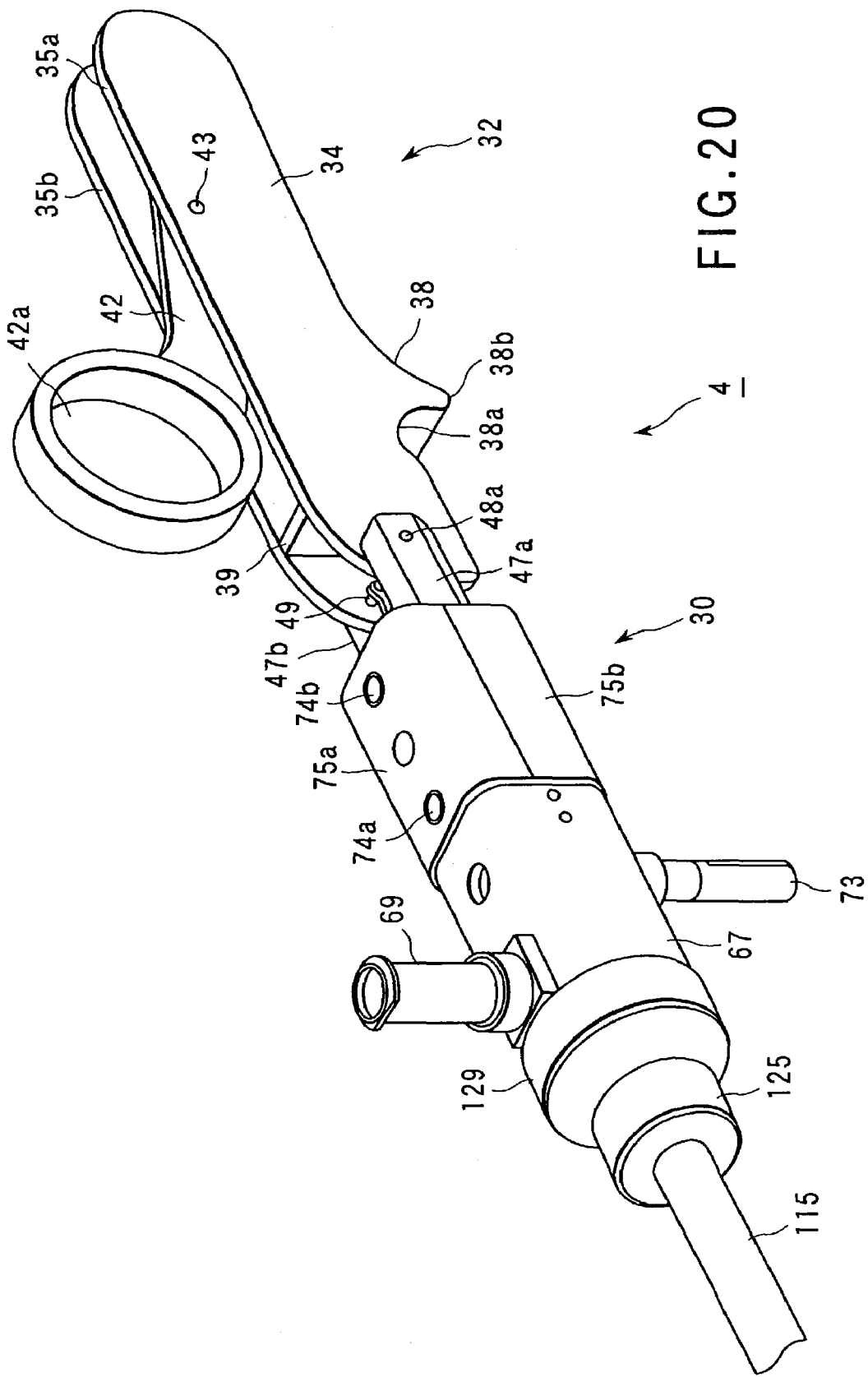
FIG. 20 is a perspective view of the operation section seen from above in the surgical instrument of the first embodiment.

As shown in FIGS. 16 to 20, especially FIGS. 16 and 20, the operation section 4 has an operation section main body 30 and a rotary handle 32. A distal end of the operation section main body 30 is integrally connected to the proximal end of the insertion section 2. The rotary handle 32 is supported by the proximal end of the operation section main body 30 so as to be rotated in one plane.

As shown in FIG. 20, the rotary handle 32 has a frame 34. The frame 34 has a structure where a pair of side plates 35a, 35b parallel to each other, a bottom plate 38, and a support section 39 for supporting the vicinity of the distal ends of the side plates 35a, 35b are integrally formed. The bottom plate 38 is formed to connect lower surfaces of the pair of side plates 35a, 35b. The bottom plate 38 is supported by fingers other than a thumb during an operation by an operator. In the bottom plate 38, a recess 38a and a finger holding portion 38b are formed to hold an index finger. The finger holding portion 38b is formed continuously from the recess 38a to project between the index finger and a middle finger. Accordingly, when the operator grips the rotary handle 32 to operate the tool, the index finger is held not only in the recess 38a but also by the finger holding portion 38b.

The side plates 35a, 35b pivotally support a proximal end of an opening/closing handle 42 which is rotated with respect to the rotary handle 32 to be opened/closed. That is, the side plates 35a, 35b and the proximal end of the opening/closing handle 42 are connected by a first rotary pin 43 pivotally supported orthogonally to an axial direction of the rotary handle 32. The opening/closing handle 42 is extended obliquely upward from the first rotary pin 43 (proximal end of the opening/closing handle 42) toward the distal end of the rotary handle 32. That is, the opening/closing handle 42 is extended from the proximal end of the opening/closing handle 42 so that the distal end can be separated from the bottom plate 38. A handle ring 42a is disposed in the distal end of the opening/closing handle 42, which the operator inserts his thumb to operate during the operation. The handle ring 42a is disposed in a position to be easily opened/closed for the rotary handle 32 when the operator supports the bottom plate 38, and puts his thumb on the handle ring 42a to grip the rotary handle. The handle ring 42a is disposed not on the proximal end of the opening/closing handle 42 but on the distal end side of the rotary handle 32. Thus, an opening/closing (rotational) direction of the thumb with respect to the index finger when the rotary handle 32 of the operation section 4 is gripped by one hand coincides with an opening/closing (rotational) direction of the opening/closing handle 42 with respect to the rotary handle 32. Therefore, the operator can easily open/close the opening/closing handle 42 with one hand.

As shown in FIGS. 16 to 19, especially FIG. 16, the operation section main body 30 is firmed in the axial direction of the insertion section 2. This operation section main body 30 has a cylindrical shape. The first and second driving rods 10, 11 extended further rearward from the proximal end of the insertion section 2 are inserted through the operation section main body 30. The proximal ends of the first and second driving rods 10, 11 are further extended rearward from the proximal end of the operation section main body 30, and positioned to be exposed to the outside of the operation section main body 30. The first driving rod 10 is arranged lopsidedly downward from the center axis of the insertion section 2 even in the operation section main body 30. The second driving rod 11 is arranged in the vicinity of the center axis of the insertion section 2 in the up-and-down direction.

Figure 21:
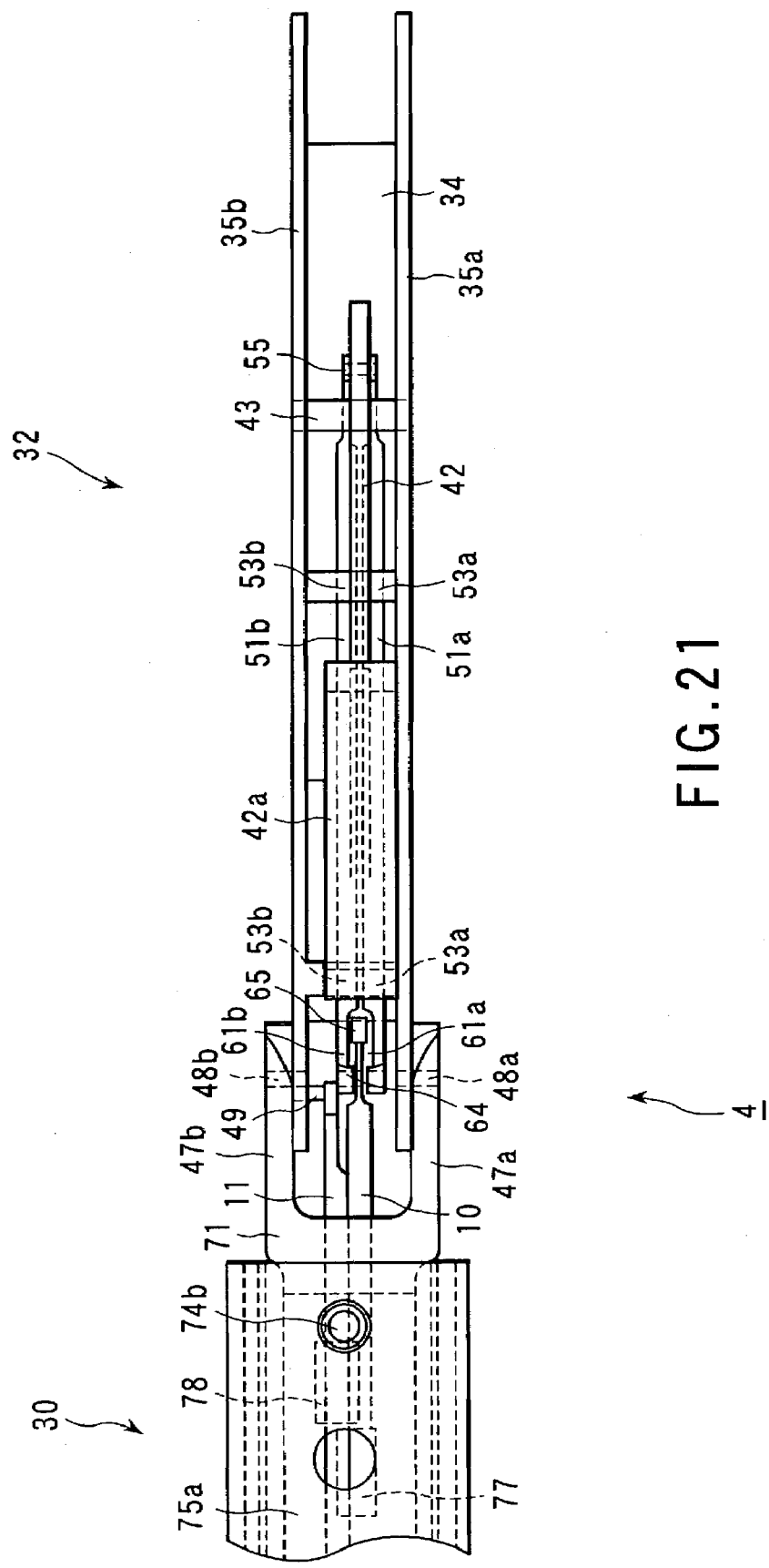
FIG. 21 is a top view of the operation section in the surgical instrument of the first embodiment.

As shown in FIGS. 20 and 21, in the proximal end of the operation section main body 30, a pair of arms 47a, 47b are extended to a rear side of the operation section main body 30. The arms 47a, 47b and the distal end of the rotary handle 32 are connected by second rotary pins 48a, 48b. The second rotary pins 48a, 48b are orthogonal to the axial direction of the insertion section 2, and extended in the left-and-right direction. Accordingly, the rotary handle 32 can be rotated in one plane with respect to the operation section main body 30 pivotally around the second rotary pins 48a, 48b.

As shown in FIG. 21, the proximal end of the second driving rod 11 inserted through the operation section main body 30 is connected to the distal end of the rotary handle 32 by a first connection pin 49 extended in the left-and-right direction. When the rotary handle 32 is rotated with respect to the operation section main body 30 pivotally around the second rotary pins 48a, 48b, the first connection pin 49 of the proximal end of the second driving rod 11 is moved associatively with the rotation of the rotary handle 32. Thus, the rotation of the rotary handle 32 is accompanied by the movement of the second driving rod 11 back and forth in the insertion section 2 and the operation section main body 30.

The rotary handle 32 has first connection members 51a, 51b between the side plates 35a, 35b of the frame 34. The first connection members 51a, 51b are made of rigid metals, e.g., stainless materials. Through-holes 53a, 53b are formed in the frame 34 in the distal and proximal end directions (longitudinal direction axis) of the rotary handle. The connection members 51a, 51b are supported by the through-holes 53a, 53b to be permitted to move back and forth in the longitudinal direction axis of the rotary handle 32, but regulated to move up-and-down and left-and-right.

A shown in FIGS. 16 to 19, especially FIG. 16, in the frame 34, a rotation regulation section 45 is disposed on which a part of the opening/closing handle 42 is abutted. This rotation regulation section 45 is disposed not on the finger holding portion 38b but on the proximal end side of the frame 34 of the rotary handle 32, and in a direction orthogonal to the axial direction of the rotary handle 32. The rotation regulation section 45 is disposed above the through-holes 53a, 53b. Thus, when the operator rotates the opening/closing handle 42 with respect to the rotary handle 32, the rotary handle 32 regulates rotation of the opening/closing handle 42 in a direction of closing later-described first and second jaws 101, 102. Thus, when the opening/closing handle 42 is opened/closed with respect to the rotary handle 32, since the amount of opening/closing is regulated, no excessive force is applied on the first connection members 51a, 51b.

As shown in FIGS. 16 to 19 and FIG. 21, especially FIGS. 16 and 21, the proximal ends of the first connection members 51a, 51b are connected to a connection pin support 56 of the opening/closing handle 41 by a second connection pin 55. The connection pin support 56 has an opening extended in a longitudinal direction of the opening/closing handle 42. The second connection pin 55 is extended in the left-and-right direction so as to move along the opening of the connection pin support 56. The opening of the connection pin support 56 is formed to regulate rotation of the opening/closing handle 42 with respect to the rotary handle 32. Thus, the second connection pin 55 can slightly move in the longitudinal direction of the opening/closing handle 42. That is, the first rotary pin 43 and the second connection pin 55 are disposed in different positions on the proximal end of the opening/closing handle 42. Therefore, when the first rotary pin 43 of the opening/closing handle 42 is rotated, the second connection pin 55 is moved along the connection pin support 56.

Second connection members 61a, 61b are disposed between distal ends of the first connection members 51a, 51b and the proximal end of the first driving rod 10. The second connection members 61a, 61b are made of rigid metals, e.g., stainless materials. Ends of the second connection members 61a, 61b are connected to the distal ends of the first connection members 51a, 51b by a third connection pin 64. The other ends of the second connection members 61a, 61b are connected to the proximal end of the driving rod 10 by a fourth connection pin 65. The third and fourth connection pins 64, 65 are extended in the left-and-right directions. When the rotary handle 32 is on the same axis as that of the operation section main body 30, the second rotary pins 48a, 48b and the third connection pin 64 are arranged on the same axis.

Both ends of each of the second connection members 61a, 61b are slotted thinner than a middle portion between both ends as in the case of later-described first and second abutment surfaces 94a, 94b (see FIGS. 22A to 22C). In the vicinity of ends of the second connection members 61a, 61b, third and fourth abutment surfaces (not shown) are formed in a manner that at least one of them is inclined in a longitudinal direction of the second connection members 61a, 61b and a normal direction orthogonal to the longitudinal direction. Accordingly, when the opening/closing handle 42 is opened/closed with respect to the rotary handle 32, the first connection members 51a, 51b are moved in the axial direction of the rotary handle 32. The second connection members 61a, 61b are moved associatively with the first connection members 51a, 51b. Then, opening/closing of the opening/closing handle 42 is accompanied by a back and forth movement of the first driving rod 10 in the insertion section 2 and the operation section main body 30. As it is supported by the proximal end of the first driving rod 10, the fourth connection pin 65 is moved back and forth only in the axial direction of the first driving rod 10. Thus, the fourth connection pin 65 is never moved to the distal end side or the proximal end side of the rotary handle 32.

As shown in FIGS. 16 to 19, especially FIG. 16, the distal end of the operation section main body 30 has a first base 66. This first base 66 is formed to be cylindrical. In the first base 66, a base main body 66a and a projected portion 66b projected forward from the base main body 66a are integrally formed. The projected portion 66b of the first base 66 has an inner hole through which at least the first and second driving rods 10, 11 can be inserted. The base main body 66a has an inner hole larger than the projected portion 66b. A step is formed in a connection portion between the base main body 66a and the projected portion 66b, which has a surface orthogonal to the axis direction of the first base 66. Thus, an outer periphery of the distal end of the first base 66 is smaller than that of the proximal end. Base ends of not-shown frames 20a, 20b disposed in the insertion section 2 are fixed to an outer peripheral surface of the projected portion 66b of the first base 66.

An insulating cylindrical second base 67 is fixed to the outer periphery of the base main body 66a of the first base 66. This second base 67 is extended more rearward than the proximal end surface of the first base 66. In the first and second bases 66, 67, through-holes are disposed to penetrate the inner holes thereof in one axis orthogonal to the axial direction of the first and second bases 66, 67. Washing ports 69 are disposed in the through-holes.

An insulating cylindrical third base 71 is disposed inside the proximal end side of the second base 67 in which the washing port 69 is disposed. An insulating airtight holding member 72 is arranged in a connection portion between the second base 67 and the third base 71. This airtight holding member 72 separates the distal end side of the second base 67 from the proximal end side to which the third base 71 is connected. The second and third bases 67, 71 have through-holes which penetrate the inner holes thereof in one axis orthogonal to the axial direction of the second and third bases 67, 71. In the through-hole, a conductive high-frequency input pin 73 made of, e.g., a stainless material, is disposed.

The high-frequency input pin 73 is disposed in a direction orthogonal to the longitudinal direction axis of the insertion section 2. According to the embodiment, the high-frequency input pin 73 and the washing port 69 are projected oppositely to each other in the axial direction of the operation section main body 30. One end of the high-frequency input pin 73 is electrically connected to the conductive first driving rod 10 in the third base 71. A not-shown high-frequency input cord is connected to the other end of the high-frequency input pin 73. When a high-frequency current (high-frequency power) is transmitted through the high-frequency input cord to the first driving rod 10, the high-frequency current is transmitted from the first driving rod 10 to the distal end of the insertion section 2, and the treatment section 3.

As shown in FIGS. 16 to 20, especially FIGS. 16 and 20, insulating first and second covers 75a, 75b are placed over an outer periphery of the third base 71. The first cover 75a is fixed to the third base 71 of the operation section main body 30 by fixing pins 74a, 74b. A second cover 75b is fixed to the third base 71 of the operation section main body 30 by fixing pins 75a, 75b. Thus, when a high-frequency current is entered from the high-frequency input pin 73, transmission of a leakage current to the operator is prevented since the first and second covers 75a, 75b are placed over the third base 71.

The aforementioned arms 47a, 47b are disposed on the proximal end of the third base 71. Accordingly, the rotary handle 32 is disposed to be rotated in one plane with respect to the operation section main body 30 (third base 71).

As shown in FIGS. 16 to 19, especially FIG. 16, the first and second driving rods 10, 11 are arranged in the operation section main body 30 to penetrate the insides of the first base 66, the second base 67, the airtight holding member 72 and the third base 71. A first insulating member 77 is fixed in the vicinity of the proximal end of the first driving rod 10, and a second insulating member 78 is fixed in the vicinity of the proximal end of the second driving rod 11.

The first and second insulating members 77, 78 electrically separate the first and second driving rods 10, 11 from each other before/after the first and second insulating members 77, 78. For connection of the first and second insulating members 77, 78, the vicinity of the proximal ends of the first and second driving rods 10, 11 is divided into two members, and the insulating members 77, 78 are fixed between the divided members. Alternatively, a male screw portion is disposed in a joined portion between the first and second driving rods 10, 11, and a female screw portion is disposed in an inner wall of each of the insulating members 77, 78. The male screw portion and the female screw portion may be engaged with each other. Thus, insulation of the high-frequency current entered from the high-frequency input pin 73 is secured more on the proximal end side of the operation section 4 than in the positions where the insulating members 77, 78 of the first and second driving rods 10, 11 are arranged.

Description will be made of the treatment section disposed on the distal end of the insertion section 2 of the surgical instrument 1 with reference to FIGS. 4 to 15 and FIG. 22.

As shown in FIGS. 4 to 15, especially FIGS. 4, 8 and 12, a tubular fourth base 81 is disposed on the distal end of the insertion section 2. This fourth base 81 is made of a metal such as a stainless material, or a hard resin material (plastic) so as to have rigidity. As shown in FIG. 8, the distal ends of the frames 20a, 20b are fixed to the proximal end of the fourth base 81. The fourth base 81 has a pair of arms 81a, 81b projected forward from the distal end of the insertion section 2.

A proximal end of a rotary cover (support) 85 is pivotally supported on the distal end (arms 81a, 81b) of the fourth base 81 through third rotary pins 82a, 82b. This rotary cover 85 is made of a rigid metal such as a stainless material. The rotary cover 85 is rotated around the third rotary pins 82a, 82b. Hereinafter, for explanation, the treatment section 3 will be described mainly by referring to FIGS. 8 to 11 which show a removed state of the rotary cover 85, and FIGS. 12 to 15 which show sections.

As shown in FIGS. 8 and 9, the upward bent distal end of the second driving rod 11 is pivotally supported on the rotary cover 85 by a fourth rotary pin 83. This fourth rotary pin 83 is disposed in parallel with the third rotary pins 82a, 82b of the fourth base 81. That is, the fourth rotary pin 83 is extended in the left-and-right directions. Since the second driving rod 11 is arranged in the vicinity of the center axis of the insertion section 2 in the up-and-down direction, the fourth rotary pin 83 disposed in the distal end of the second driving rod 11 is pivotally supported in a position offset in the axial direction of the rotary cover 85. The fourth rotary pin 83 is arranged on a side higher than the center axis of the rotary cover 85.

The fourth rotary pin 83 and third rotary pins 82a, 82b, and the first connection pin 49 and the second rotary pins 48a, 48b are arranged in parallel with each other. When the rotary handle 32 is rotated with respect to the operation section main body 30, the second rotary pins 48a, 48b, and the third rotary pins 82a, 82b hold their positions with respect to the insertion section 2. Since it is shifted in position from the second rotary pins 48a, 48b (rotational centers) (see FIG. 21), the first connection pin 49 is moved back and forth in the axial direction of the insertion section 2, and in the up-and-down direction by rotation of the rotary handle 32 with respect to the operation section main body 30. On the other hand, the fourth rotary pin 83 is shifted in position from the third rotary pins 82a, 82b (rotational centers). Since parallel states are maintained between the fourth rotary pin 83 and the third rotary pins 82a, 82b, and between the first connection pin 49 and the second rotary pins 48a, 48b, the fourth rotary pin 83 is moved back and forth in the axial direction of the insertion section 2, and in the up-and-down direction. At this time, the first driving rod 10 and a second driving rod 11 are arranged in parallel with each other. Accordingly, the rotary cover 85 is rotated around the distal end of the insertion section 2. That is, the treatment section 3 is raised with respect to the insertion section 2.

As shown in FIGS. 12 to 15, especially FIG. 12, the distal end of the first driving rod 10 which has a circular-arc outer peripheral surface is connected through a fifth connection pin 87 extended left and right to a proximal end of a third connection member (connecting rod) 88. A distal end of the third connection member 88 is connected through a sixth connection pin 89 extended left and right to a proximal end of a fourth connection member (sliding member) 90. The third and fourth connection members 88, 90 are made of conductive and rigid metals such as stainless materials. The fourth connection member 90 can slide in the rotary cover 85. A proximal end surface of the fourth connection member 90 is formed in a circular-arc shape. That is, the proximal end of the fourth connection member 90 has a shape similar to an outer peripheral surface of a disk which has an axis in a direction orthogonal to an axial direction of the fourth connection member 90.

Figure 13:
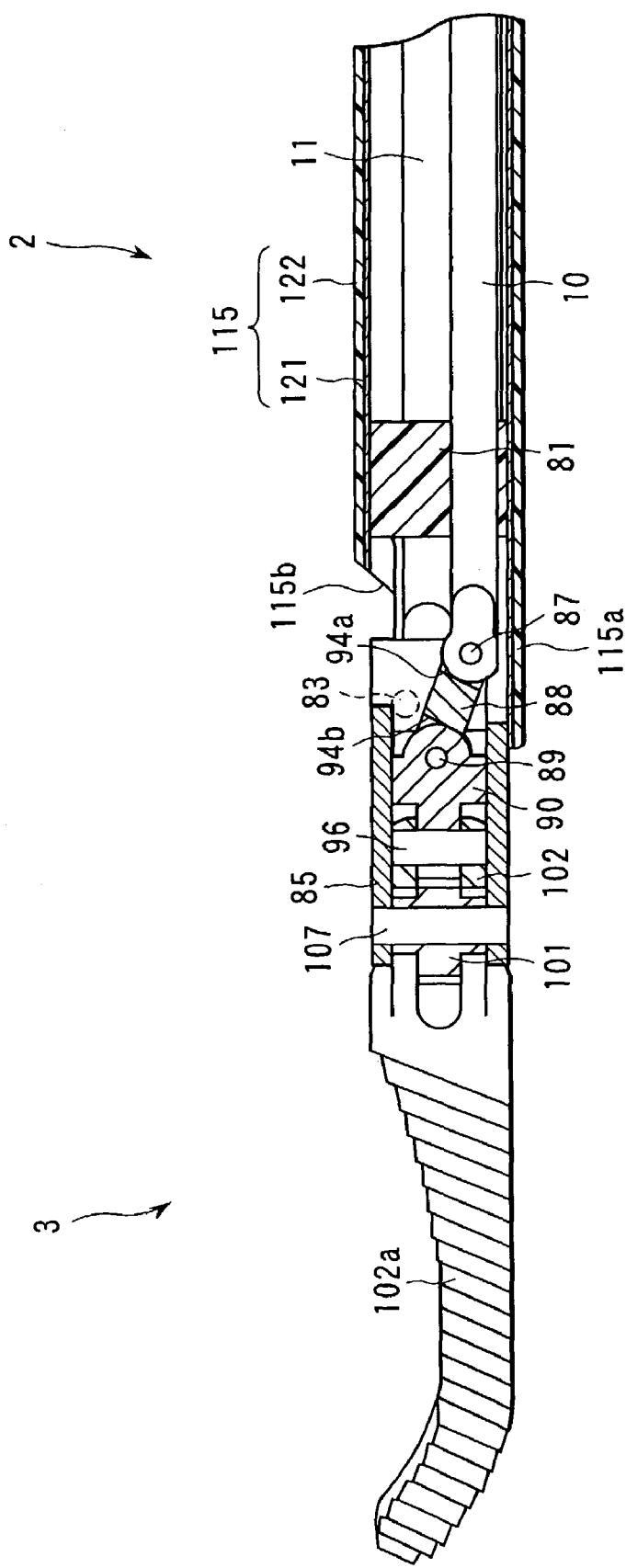
FIG. 13 is a sectional view along the line B-B of FIG. 2 showing a state where the jaw of the treatment section is opened in the surgical instrument of the first embodiment.

As shown in FIGS. 12 and 13, the fifth connection pin 87 is arranged lower than the center axis of the insertion section 2, and the sixth connection pin 89 is arranged in a position equal to or roughly equal to the center axis of the insertion section 2. Thus, the sixth connection pin 89 is disposed above the fifth connection pin 87. The third connection member 88 is disposed in a state of being inclined upward to the front in the axial direction of the first driving rod 10.

Figure 22A:
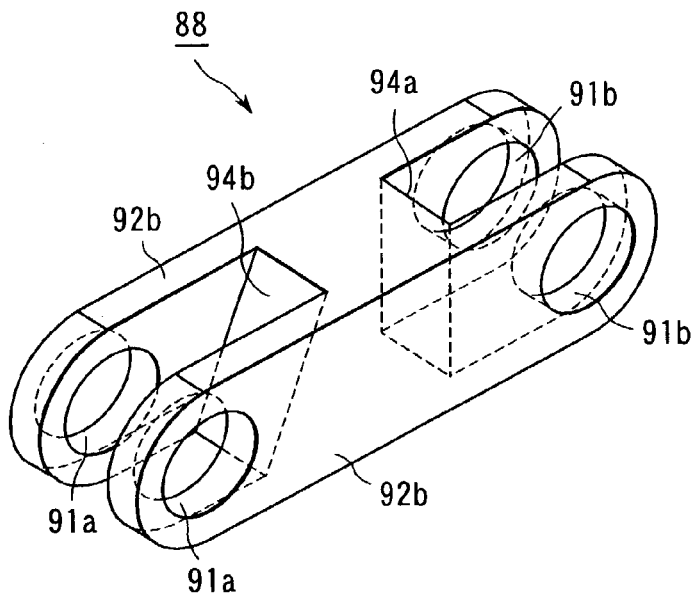
FIG. 22A is a perspective view showing a third connection member in the surgical instrument of the first embodiment.
Figure 22B:
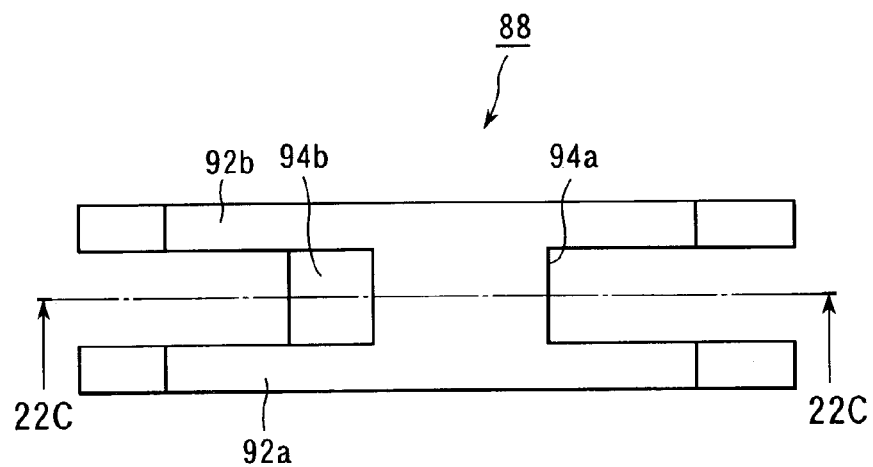
FIG. 22B is a top view showing the third connection member of FIG. 22A.
Figure 22C:
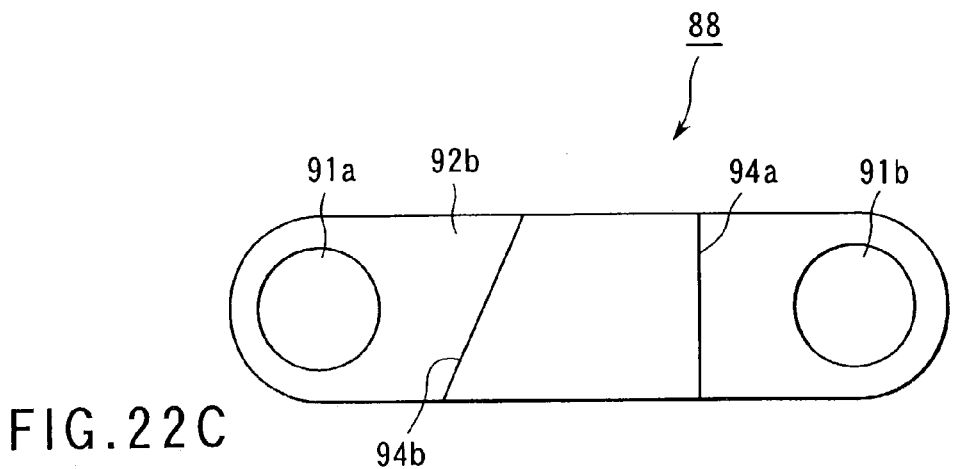
FIG. 22C is a sectional view along the line 22C-22C of FIG. 22B.
Figure 23:
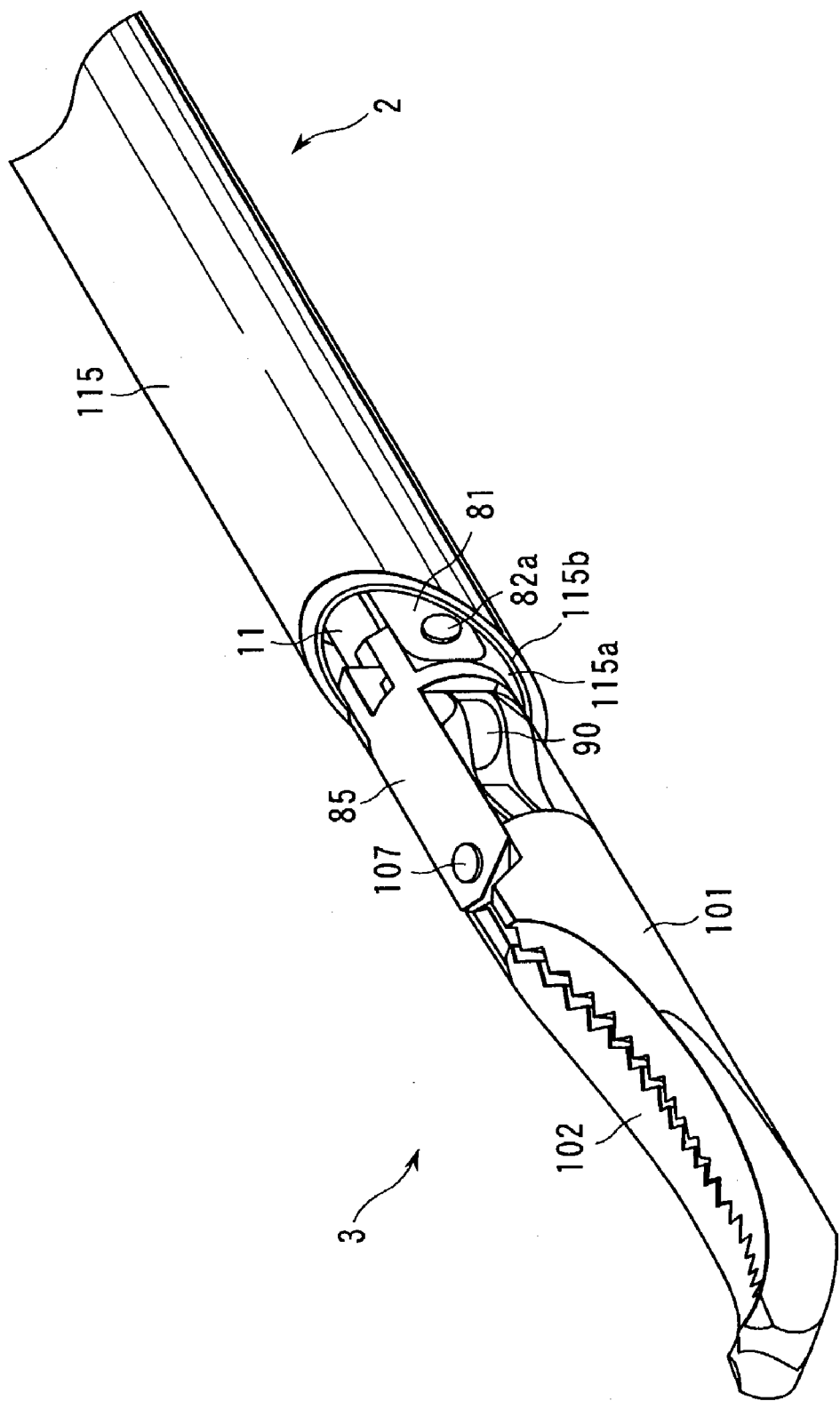
FIG. 23 is a perspective view of a state seen from above where the treatment section is set straight with respect to the insertion section in the surgical instrument of the first embodiment.

As shown in FIGS. 22A to 22C, on the distal and proximal ends of the third connection member 88, two thin and long flat plates 92a, 92b which have circular holes 91a, 91b are arranged oppositely to each other. The flat plates 92a, 92b are integrally connected between the distal and proximal ends. Accordingly, the distal and proximal ends of the third connection members 88 are formed in slotted shapes. On the proximal end side of the third connection member 88, a first abutment surface 94a is formed on which the surface of the distal end of the first driving rod 10 is always abutted. On the distal end side of the third connection member 88, a second abutment surface 94b is formed on which a surface of the proximal end of the fourth connection member 90 is always abutted. This second abutment surface 94b is inclined in the axial direction of the third connection member 88.

The surface of the distal end of the first driving rod 10 is in a state of being in line contact with the first abutment surface 94a of the third connection member 88. Since the distal end of the first driving rod 10 is abutted on the first abutment surface 94a, when the first driving rod 10 is moved back and forth in its axial direction, a force produced by the back and forth movement of the first driving rod 10 is surely transmitted to the third connection member 88.

The surface of the proximal end of the fourth connection member 90 is in a state of being in line contact with the second abutment surface 94b of the third connection member 88. When the force of the back and forth movement of the first driving rod 10 is transmitted to the third connection member 88, the force of the back and forth movement of the first driving rod 10 is surely transmitted through the third connection member 88 to the fourth connection member 90.

Figure 14:
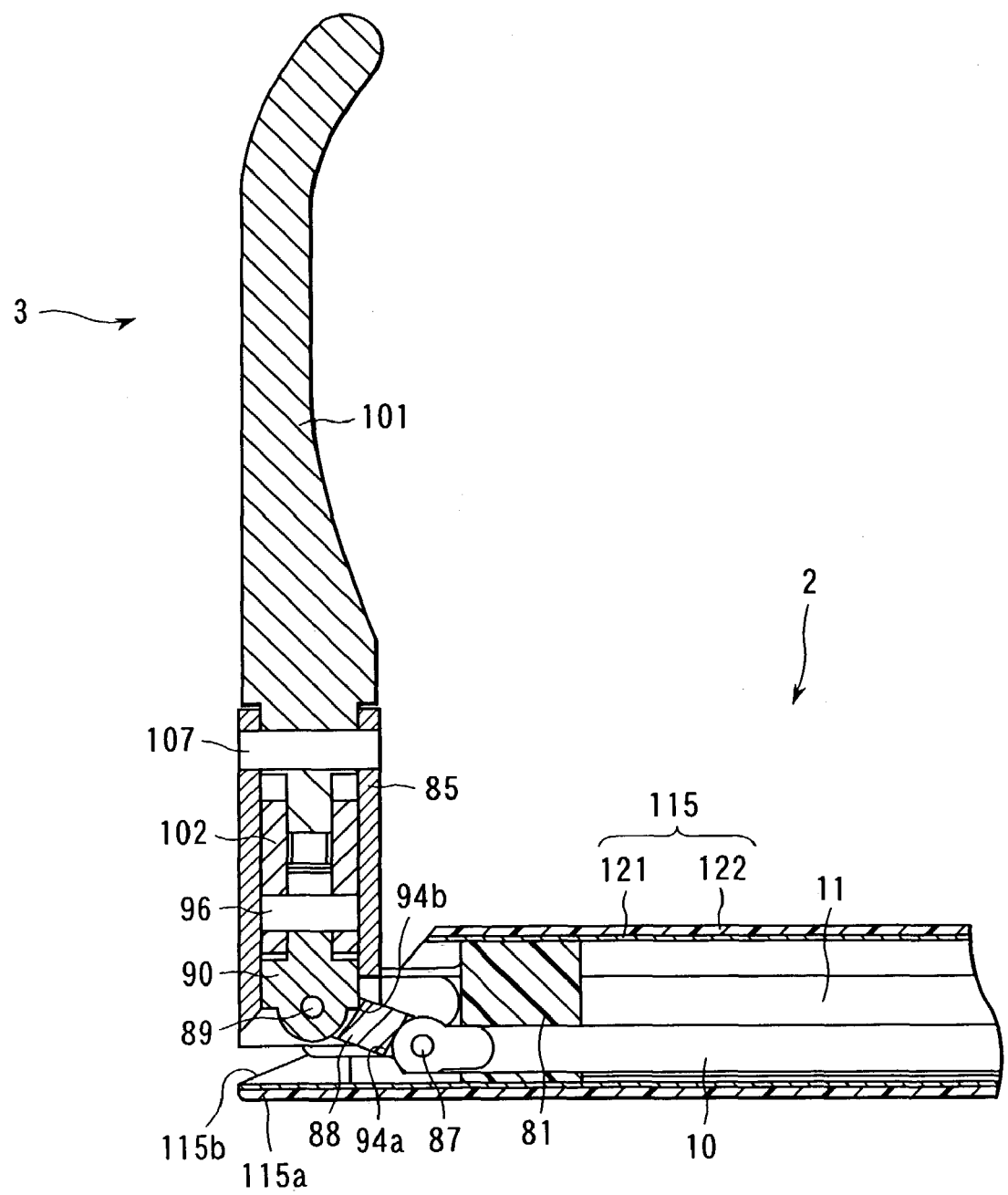
FIG. 14 is a sectional view along the line B-B of FIG. 2 showing a state where the treatment section is raised with respect to the insertion section in the surgical instrument of the first embodiment.
Figure 15:
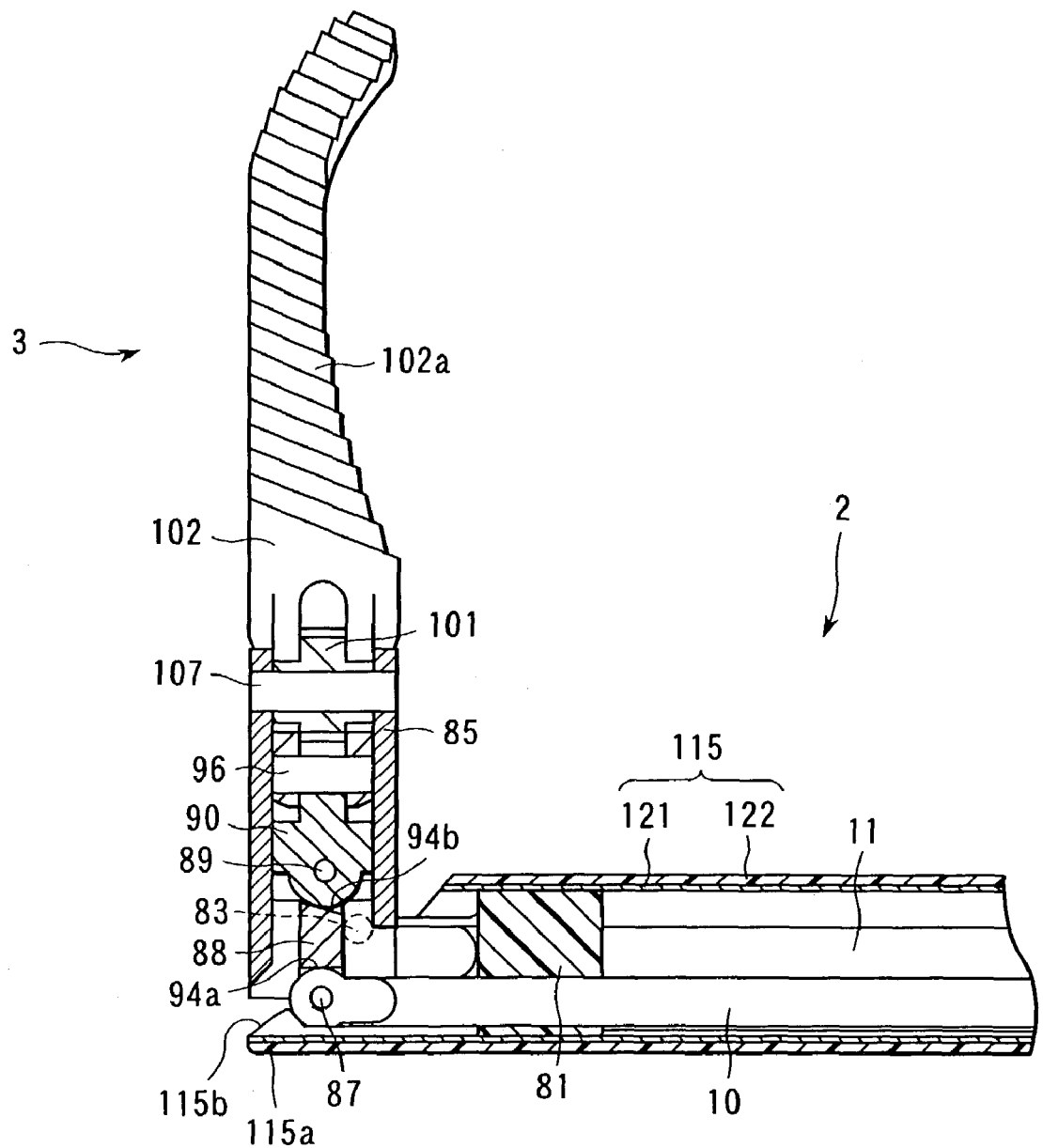
FIG. 15 is a sectional view along the line B-B of FIG. 2 showing a state where the treatment section is raised and the jaw is opened in the surgical instrument of the first embodiment.

That is, the first abutment surface 94a of the third connection member 88 is disposed to push out the fourth connection member 90 forward and upward when the first driving rod 10 moves back and forth. Since the distal end surface of the first driving rod 10 is formed in a circular-arc shape, it is difficult for friction resistance to be increased between the distal end of the first driving rod 10 and the first abutment surface 94a of the third connection member 88. When the treatment section 3 is rotated as shown in FIGS. 14 and 15, the second abutment surface 94b of the third connection member 88 can bring a direction of a normal force applied on the proximal end and the second abutment surface 94b of the fourth connection member 90 close to the axial direction of the treatment section 3.

That is, the third connection member 88 is disposed to be inclined between the distal end of the first driving rod 10 and the fourth connection member 90, and comprises the first and second abutment surfaces 94a, 94b. Thus, the third connection member 88 can assist a force applied to push up the fourth connection member 90 when the treatment section 3 has been rotated in the axial direction of the insertion section 2.

As shown in FIGS. 8 to 15, especially FIGS. 8 and 12, the distal end of the fourth connection member 90 which can slide inside the rotary cover 85 is pivotally supported by a seventh connection pin 96. This seventh connection pin 96 is extended in a direction orthogonal to the proximal end (sixth connection pin 89) of the fourth connection member 90, i.e., in the up-and-down direction. Of first and second jaws 101, 102 constituting a tip-tool, a proximal end of the second jaw 102 is pivotally supported by the seventh connection pin 96. Accordingly, the distal end of the fourth connection member 90 is connected to the proximal end of the second jaw 102 by the seventh connection pin 96.

The proximal end of the second jaw 102 is bent in a direction shifted from the axial direction of the treatment section 3 from a position connected by the seventh connection pin 96 toward the front. The second jaw 102 is formed to be parallel with the axial direction of the treatment section 3 again from the midway toward the front. The first jaw 101 is supported on the proximal end of the second jaw 102 which becomes parallel to the axial direction of the treatment section 3. This first jaw 101 is pivotally supported on the second jaw 103 by a first opening/closing pin 105 extended in the up-and-down direction. The first jaw 101 is bent in a direction shifted from the axial direction of the treatment section 3 from a position connected by the first opening/closing pin 105 toward the front. The bending direction is opposite the bending direction of the proximal end of the second jaw 102. The first jaw 101 is formed to be parallel with the axial direction of the treatment section 3 from the midway toward the front. Thus, the pair of jaws 101, 102 is opened/closed roughly symmetrically in the axial direction of the treatment section 3.

Figure 5:
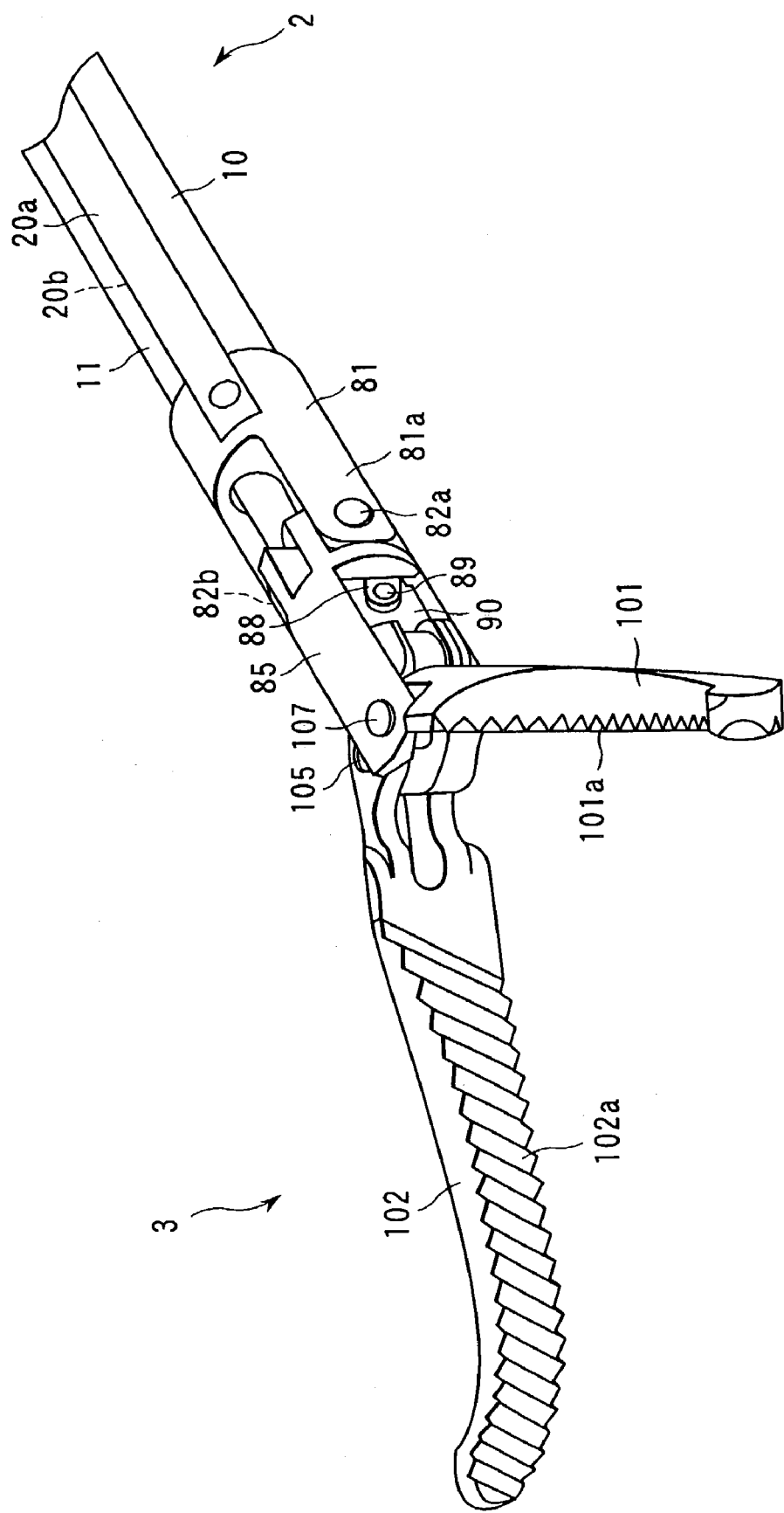
FIG. 5 is a perspective view of a state seen from above where a jaw of the treatment section is opened while the sheath is removed from the insertion section in the surgical instrument of the first embodiment.

As shown in FIGS. 4 to 11, especially FIGS. 5 and 9, the first and second jaws 101, 102 are disposed in opposite directions with respect to grip surfaces 101a, 102a symmetrically in the axial direction of the treatment section 3. When necessary, recessed and projected portions are formed in the grip surfaces 101a, 102a.

Upper surfaces of the first and second jaws 101, 102 are bent with respect to center axes thereof. The bending directions of the jaws 101, 102 coincide with a rotation direction of the treatment section 3 as shown in FIG. 12. That is, in the first and second jaws 101, 102, one (upper surface) of surfaces adjacent to the grip surfaces 101a, 102a is set in a direction different from that of the proximal end. Specifically, upper surfaces of the tips of the jaws 101, 102 are directed upward to the back in FIG. 12, and upper surfaces adjacent to the proximal ends of the portions having the grip surfaces 101a, 102a are directed upward to the front in FIG. 12. The distal ends and the proximal ends adjacent to the portions having the grip surfaces 101a, 102a are formed to be smooth.

A second opening/closing pin 107 is disposed on the proximal end of the portion having the grip surface 101a of the first jaw 101 to project in the up-and-down direction. As shown in FIGS. 4 to 7, especially FIG. 4, the second opening/closing pin 107 is supported by the rotary cover 85. The rotary cover 85 defines a distance between the third rotary pins 82a, 82b of the fourth base 81 and the second opening/closing pin 107. Inside the rotary cover 85, the fourth connection member 90 and the seventh connection pin 96 of the distal end of the fourth connection member 90 are disposed to slide. Thus, the proximal end of the second jaw 102 is also housed to slide in the rotary cover 85.

The first and second jaws 101, 102 are made of conductive and rigid metals such as stainless materials. Accordingly, a high-frequency current can be conducted from the high-frequency pin 73 shown in FIG. 16 to the first driving rod 10, the third connection member 88, the fourth connection member 90, the second jaw 102 and the first jaw 101. Thus, the biomedical tissue can be treated with a high frequency by the first and second jaws 101, 102.

Each of the distal ends and the proximal ends of the first and second driving rods 10, 11, and the first to fourth connection members 51, 61, 88, 90 has a circular-arc surface. The second connection members 61a, 61b disposed in the operation section 4 and the third connection member 88 disposed in the treatment section 3 are in a positional relation of both sides in a parallelogram link mechanism where the first driving rod 10 is a long side. The first connection members 51a, 51*b* and the fourth connection member 90 are arranged in point-symmetrical positions with respect to a middle point of the first driving rod 10.

The surgical instrument 1 of the foregoing constitution further has a sheath 5 in the insertion section 2.

As shown in FIGS. 1 to 3, FIGS. 23 to 29, especially FIG. 2, the frames 20*a*, 20*b* of the insertion section 2 of the surgical instrument 1 of the embodiment is covered with the sheath 5. As shown in FIG. 1, the sheath 5 has a thin and long sheath insertion section 115 to cover the frames 20*a*, 20*b*, and a sheath fixing section 116 detachable from the proximal end (distal end of the operation section 4) of the insertion section 2.

As shown in FIG. 3, the sheath insertion section 115 has a dual structure. Specifically, the sheath insertion section 115 is formed by combining a circular and tubular second sheath 122 with an outer periphery of a circular and tubular first sheath 121. The first sheath 121 of the inner side is made of a rigid material, e.g., a metal such as a stainless material. The second sheath 122 of the outer side is made of an insulating material such as PTFE. The entire outer peripheral surface of the first sheath 121 is covered with the second sheath 122. An outer wall surface of the first sheath 121 and an inner wall surface of the second sheath 122 are bonded to each other to be integrated.

Figure 17:
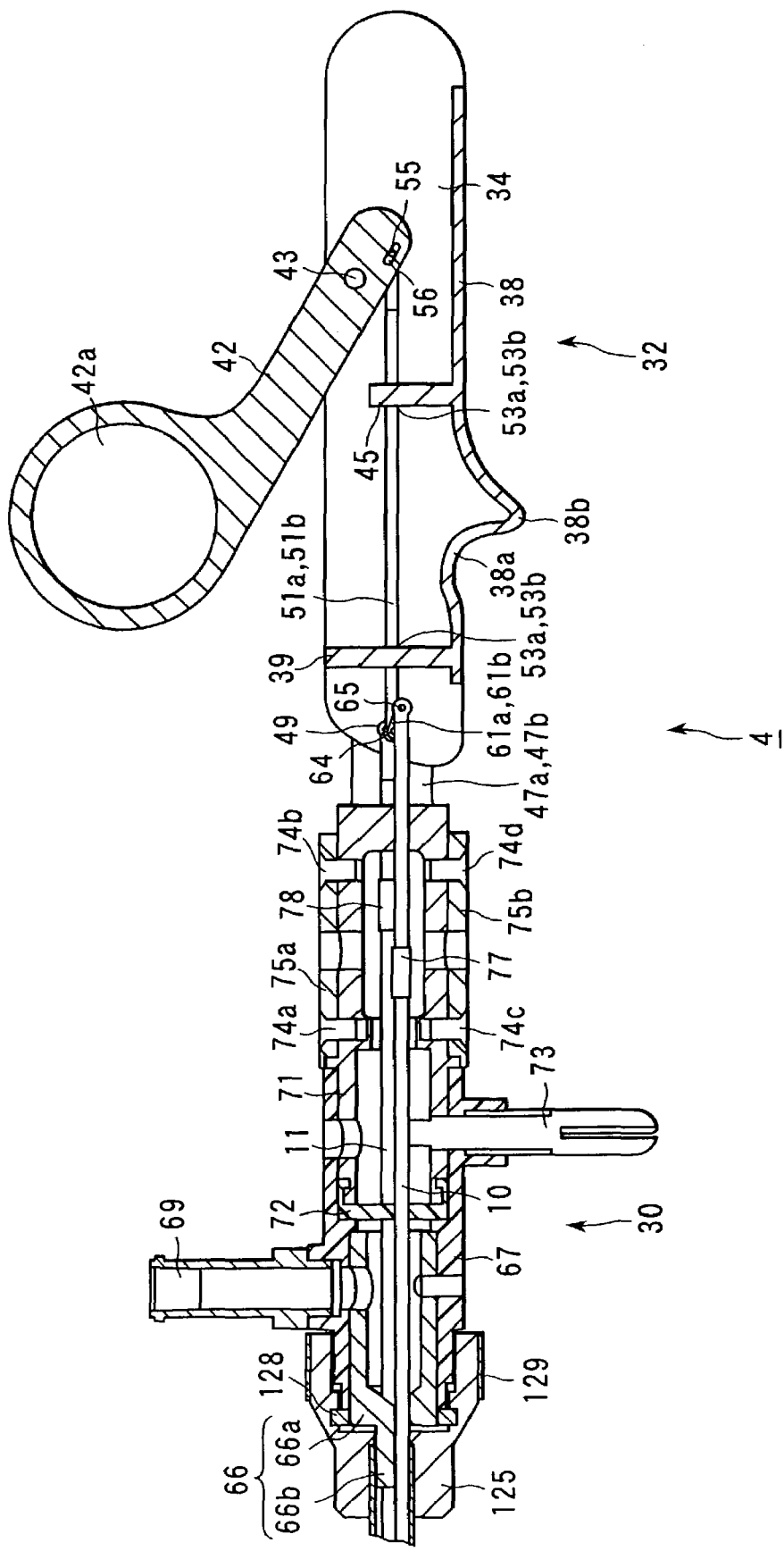
FIG. 17 is a sectional view along the line B-B of FIG. 2 showing a state where the opening/closing handle of the operation section is opened with respect to the rotary handle in the surgical instrument of the first embodiment.

As shown in FIG. 20, a sheath flange 125 is disposed in a sheath fixing section 116 of the proximal end of such a sheath insertion section 115. As shown in FIGS. 17 and 19, the sheath flange 125 is formed to fit to the first and second bases 66, 67. In the recess on the inner peripheral surface of the sheath flange 125, an airtight seal 128 is arranged to seal the first and second bases 66 and 67 from each other when they are fixed to the insertion section 2. For the airtight seal 128, an O-ring made of an elastic material such as rubber is used. The sheath flange 125 is always pressed toward the outside of a diameter direction of the proximal end by the airtight seal 128 when it is fixed to the insertion section 2. The airtight seal 128 is disposed in such a manner as to hermetically seal a side after the position of the airtight seal 128.

As shown in FIG. 1, on the base 67 disposed in the operation section main body 30 of the operation section 4 to which the sheath 5 is fixed, a lock pin 127 is projected to the side in the axial direction of the insertion section 2. A lock groove 125*a* is disposed on the side of the sheath flange 125 to be freely engaged with/disengaged from the lock pin 127. Accordingly, a proximal end (sheath fixing section 116) of the sheath 5 is attached to/detached from the first and second bases 66, 67 by a bayonet structure. That is, the sheath 5 is fixed to the insertion section 2 of the surgical instrument 1. As shown in FIGS. 1 and 20, a flange cover 129 is fixed to a portion of the sheath flange 125 which has the lock groove 125*a*. In other words, the lock groove 125*a* of the sheath flange 125 is covered to the outer peripheral surface with the flange cover 129. Accordingly, the lock groove 125*a* is in a state of being hidden from the sheath fixing section 116.

As shown in FIGS. 12 to 15, especially FIG. 14, a distal end (distal ends of the first and second sheaths 121, 122) of the sheath insertion section 115 is inclined in section. The distal end of the sheath insertion section 115 has an extended portion 115*a* extended to a position where an end is opposite by 180°. This extended portion 115*a* is disposed on the backside of a rotational area of the treatment section 3 in a state where the sheath 5 is fixed to the insertion section 2. The extended portion 115*a* is formed so that at least the proximal end of the rotary cover 85 can be covered when the treatment section 3 is arranged on the same axis as that of the insertion section 2. An end 115*b* of the extended portion 115*a* is formed in, e.g., an elliptical shape.

The extended portion 115*b* is disposed in the distal end of the sheath 5 so as not to interfere with rotation of the treatment section 3 with respect to the insertion section 2. The extended portion 115*a* prevents contact of the rotary cover 85 with the vicinity of the proximal end of the treatment section 3, e.g., portions other than a target portion during the operation. The extended portion 115*a* prevents contact of the vicinity of the proximal end of the treatment section 3 with unintended portions. Thus, a high-frequency treatment of unintended portions is prevented by the extended portion 115*a*.

Description will be made of an operation of the surgical instrument 1 constituted in the foregoing manner.

The pair of jaws 101, 102 of the treatment section 3 of the surgical instrument 1 is closed, and the treatment section 3 is set in the same direction as that of the insertion section 2. The sheath 5 is fixed to the insertion section 2 where the first and second driving rods 10, 11 of the surgical instrument 1 are exposed. The sheath fixing section 116 of the proximal end of the sheath 5 is abutted on the first and second bases 66, 67 of the distal end of the operation section 4. When the lock pin 127 of the second base 67 is engaged with the lock groove 125*a* of the sheath flange 125, the airtight seal 128 prevents infiltration of gas and liquid from the side before the position of the airtight seal 128 to the side after the same.

The operator inserts his thumb into the handle ring 42*a* of the opening/closing handle 42, inserts his index finger in the recess 38*a* and the finger holding portion 38*b* of the bottom plate 38 of the rotary handle 32, and supports the bottom plate 38 by the remaining fingers. In this way, the operator grips the rotary handle 32.

As shown in FIG. 2, the insertion section 2 of the surgical instrument 1 and the rotary handle 32 of the operation section 4 are arranged on the same axis. The opening/closing handle 42 is closed with respect to the rotary handle 32. From this state, the opening/closing handle 42 is rotated with respect to the rotary handle 32. That is, the opening/closing handle 42 is opened with respect to the rotary handle 32 around the first rotary pin 43 from a state shown in FIG. 16 to a state shown in FIG. 17.

As the first connection members 51*a*, 51*b* of the rotary handle 32 are regulated in position, the second connection pin 55 of the proximal end of the opening/closing handle 42 is moved from the proximal end of the connection pin support 56 toward the distal end. The movement of the second connection pin 55 is accompanied by movements of the first connection members 51*a*, 51*b* toward the distal end of the rotary handle 32. When the first connection members 51*a*, 51*b* move toward the distal end of the rotary handle 32, the second connection members 61*a*, 61*b* are moved toward the distal end of the rotary handle 32 by the third connection pin 64. When the second connection members 61*a*, 61*b* move toward the distal end of the rotary handle 32, the first driving rod 10 is advanced while keeping the same height by the fourth connection pin 65.

As shown in FIGS. 12 and 13, the distal end of the first driving rod 10 advances along the center axis of the insertion section 2 to the treatment section 3 side. Upon the advancement of the first driving rod 10 along the center axis of the insertion section 2 to the treatment section 3 side, the third connection member 88 is advanced by the fifth connection pin 87 pivotally supported on the distal end of the first driving rod 10. Upon the advancement of the third connection member 88, the fourth connection member 90 is advanced in the rotary cover 85 by the sixth connection pin 89. Upon the advancement of the fourth connection member 90, the seventh connection pin 96 advances in the rotary cover 85.

As shown in FIGS. 4 and 5, the movement of the second opening/closing pin 107 is regulated by the rotary cover 85. Accordingly, as shown in FIG. 8 and 9, the first opening/closing pin 105 moves to the side by using the seventh connection pin 96 as a supporting point. The movement of the first opening/closing pin 105 is accompanied by rotation of the second jaw 102 to the side by using the seventh connection pin 96 as a supporting point. Since the movement of the second opening/closing pin 107 is regulated, the first jaw 101 is opened with respect to the second jaw 102 associatively with the movement of the first opening/closing pin 105.

As shown in FIG. 16 and 17, the second driving rod 11 is unaffected by the rotation of the opening/closing handle 42, and thus unmoved. Therefore, a force for rotating the rotary cover 85 is not transmitted at the distal end of the second driving rod 102.

Figure 24:
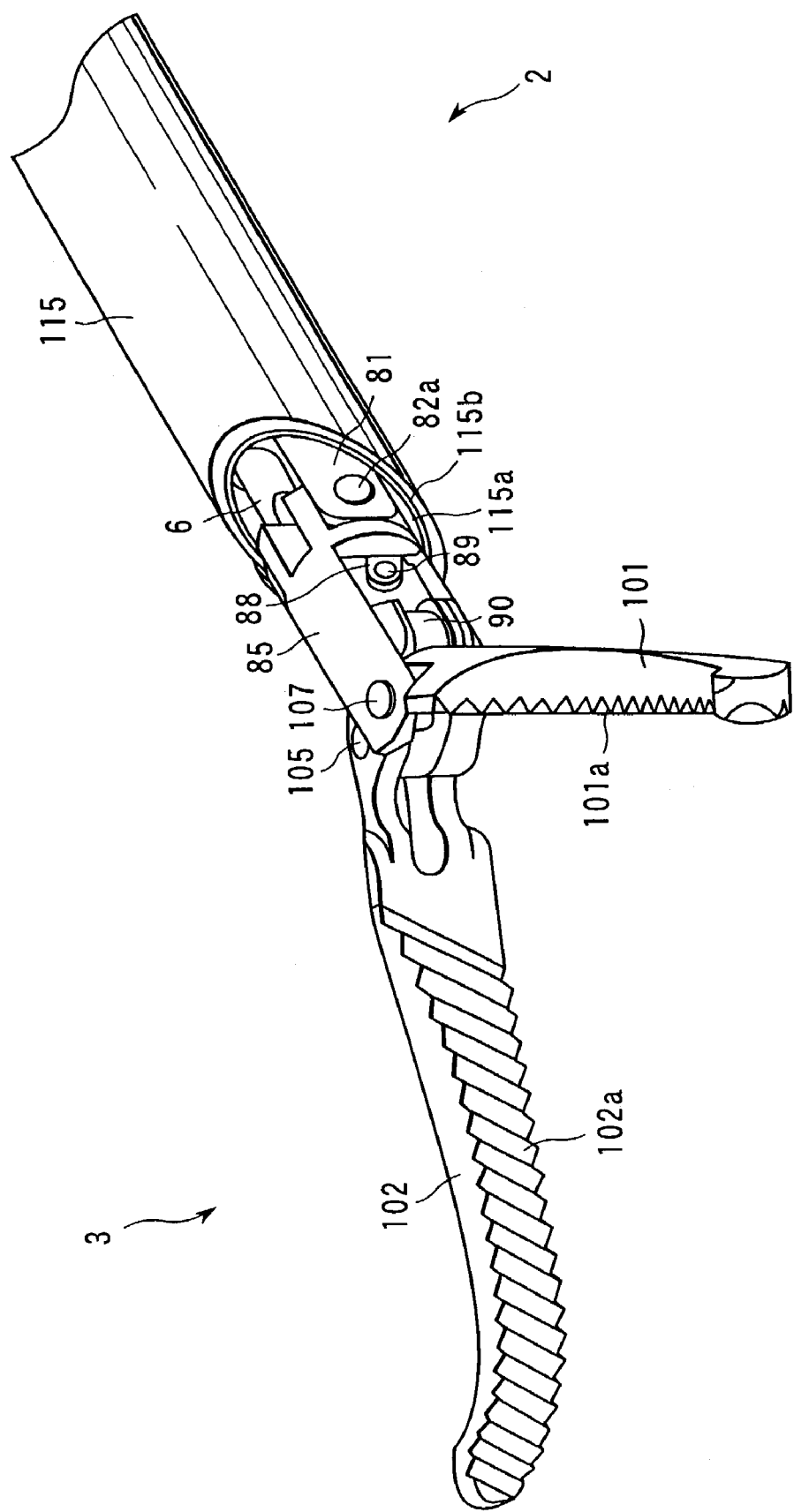
FIG. 24 is a perspective view of a state seen from above where the jaw of the treatment section is opened in the surgical instrument of the first embodiment.
Figure 27:
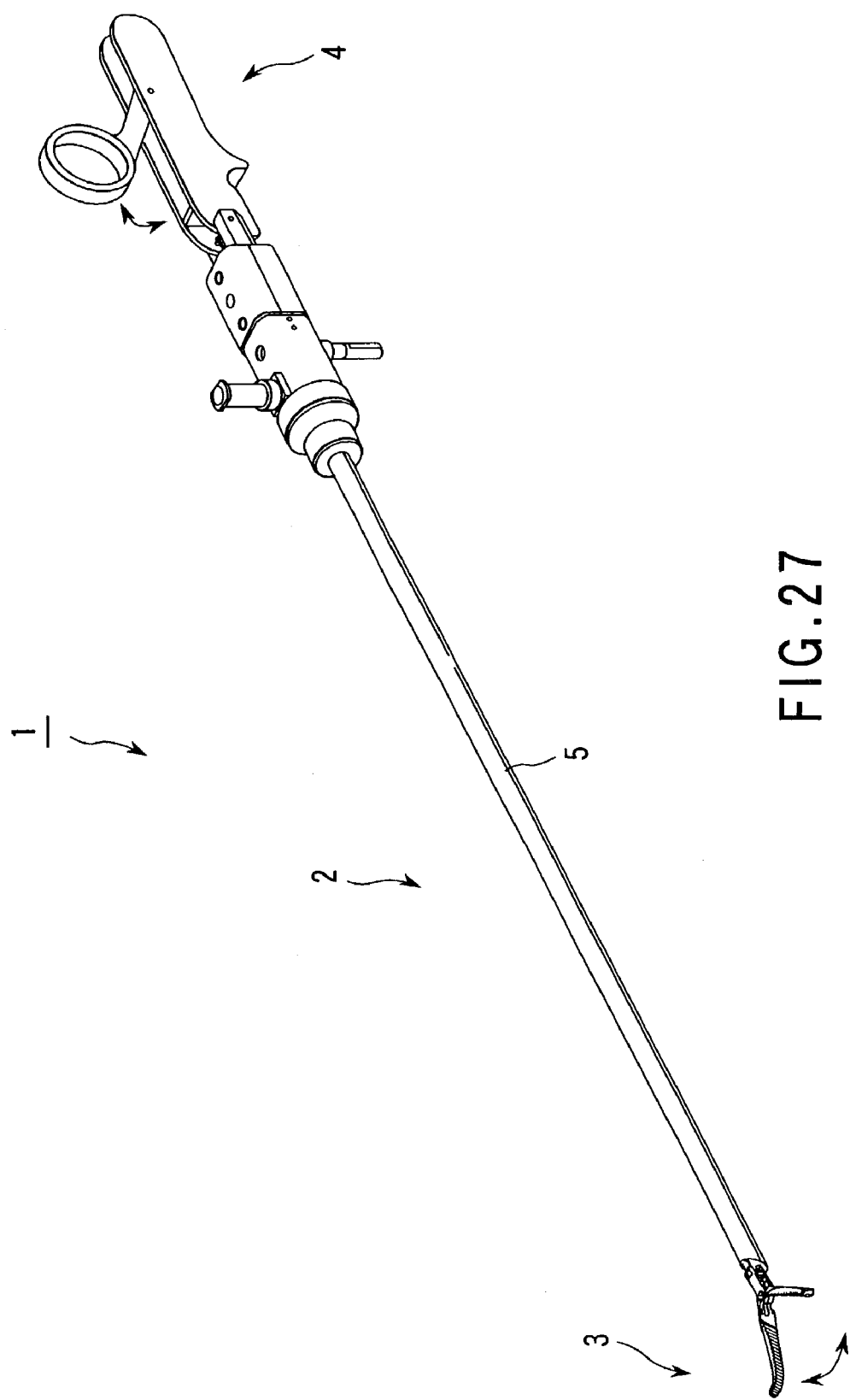
FIG. 27 is a perspective view of a state seen from above where the opening/closing handle is opened with respect to the rotary handle of the operation section to open the jaw of the treatment section, showing the entire constitution of the surgical instrument of the first embodiment.

That is, when the opening/closing handle 42 is rotated upward around the first rotary pin 44 from the state of the surgical instrument 1 shown in FIG. 1, as shown in FIGS. 24 and 27, the first and second jaws 101, 102 of the treatment section 3 are symmetrically opened in the axis of the treatment section 3.

When the rotational amount of the opening/closing handle 42 with respect to the rotary handle 32 is maintained within a predetermined amount, the first and second jaws 101, 102 are opened corresponding to the rotational amount.

As shown in FIG. 2, the insertion section 2 of the surgical instrument 1 and the rotary handle 32 of the operation section 4 are arranged on the same axis again. The opening/closing handle 42 is closed with respect to the rotary handle 32. The rotary handle 32 is rotated in one plane from this state until the rotary handle 32 of the operation section 4 is directed downward by 90° (see FIG. 18) with respect to the insertion section 2. That is, from the state shown in FIG. 16 to the state shown in FIG. 18, the rotary handle 32 is rotated downward with respect to the operation section main body 30 by using the second rotary pins 48a, 48b disposed on the proximal end of the operation section main body 30 and the distal end of the rotary handle 32 as supporting points.

As shown in FIGS. 16 and 18, since the opening/closing handle 42 is unmoved and not rotated with respect to the rotary handle 32, the first connection members 51a, 51b are unmoved with respect to the rotary handle 32. In this case, as shown in FIG. 21, since the second rotary pins 48a, 48b of the distal end of the rotary handle 32 and the third connection pin 64 are arranged on the same axis, the second connection members 61a, 61b are not moved. Thus, the second connection members 61a, 61b maintain the state shown in FIG. 16 (see FIG. 18). The first driving rod 10 is unmoved with respect to the operation section main body 30, the insertion section 2 and the treatment section 3. Thus, no opening/closing forces are transmitted to the first and second jaws 101, 102 of the treatment section 3.

As shown in FIGS. 16 and 18, the first connection pin 49 is located before the second rotary pins 48a, 48b. Since the second rotary pins 48a, 48b of the distal end of the rotary handle 32 and the first connection pin 49 of the proximal end of the second driving rod 11 are on difference axes, the first connection pin 49 of the proximal end of the second driving rod 11 is moved associatively with the rotation of the rotary hand 32. Since the first connection pin 49 is supported by the rotary handle 32, when the rotary handle 32 is rotated with respect to the operation section main body 30, the first connection pin 49 is pulled to the proximal end side of the insertion section 2 associatively with the rotation of the rotary handle 32. The pulling of the first connection pin 49 to the proximal end side of the insertion section 2 is accompanied by pulling of the proximal end of the second driving rod 11 to the proximal end side of the insertion section 2.

As shown in FIGS. 12 and 14, the bent distal end of the second driving rod 11 arranged above the center axis of the insertion section 2 is retreated in the axial direction of the insertion section 2 to the operation section 4 side. The force caused by the retreat of the second driving rod 11 is transmitted to the rotary cover 85 through the fourth rotary pin 83 (see FIG. 8) pivotally supported on the distal end of the second driving rod 11. At this time, the second driving rod 11 is parallel with the first driving rod 10, and moved up and down in the second through-hole 25b (see FIG. 3) of the regulation members 21a to 21c. That is, when the rotary handle 32 is rotated with respect to the operation section main body 30, the second driving rod 11 is moved in the axial direction of the insertion section 2, and in the up-and-down direction. The fourth rotary pin 83 is moved with respect to the third rotary pins 82a, 82b (rotational centers) in the same orbit as that in which the first connection pin 49 is moved with respect to the second rotary pins 48a, 48b (rotational centers). Accordingly, the rotary cover 85 is raised with respect to the insertion section 2.

Figure 25:
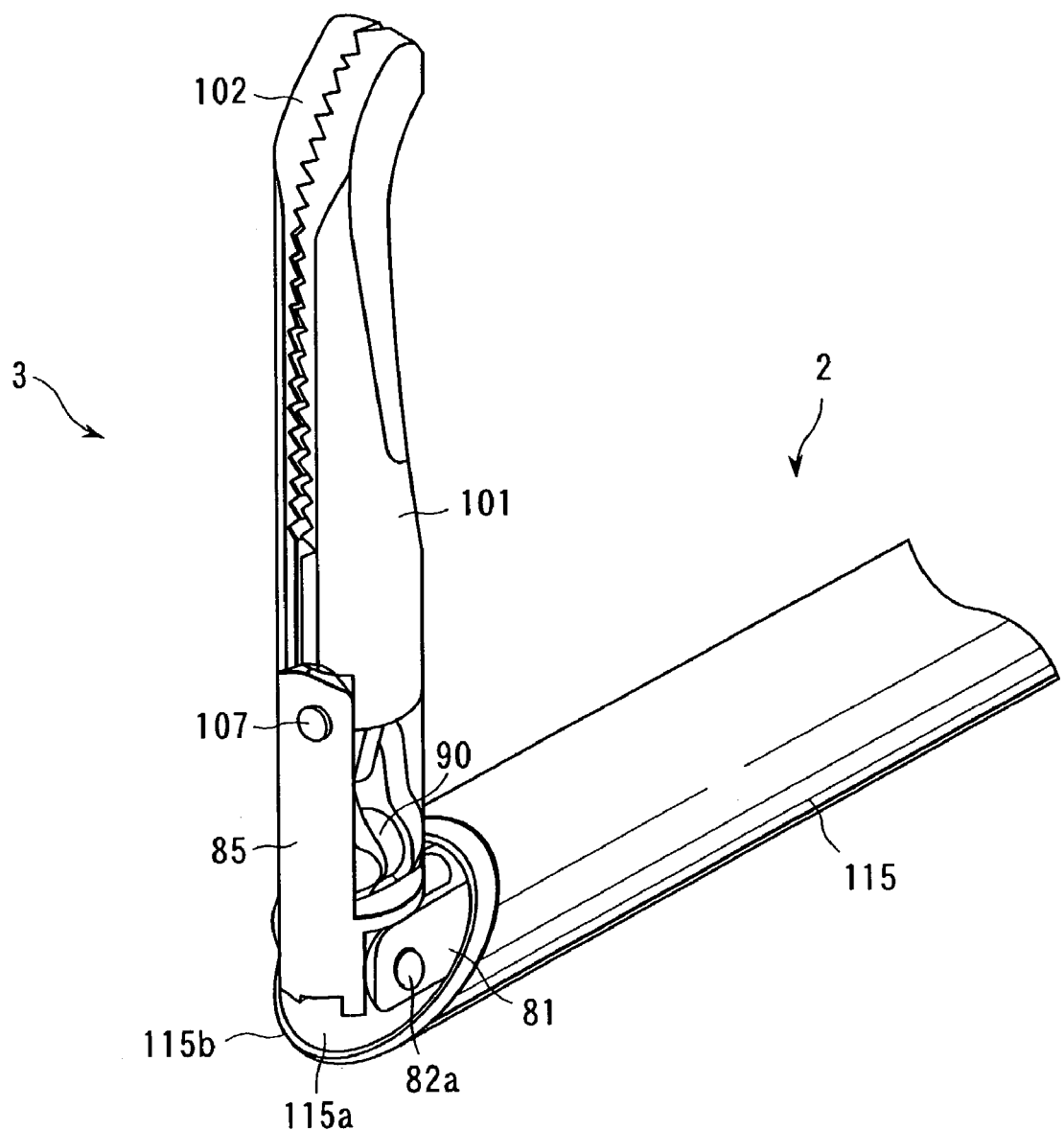
FIG. 25 is a perspective view of a state seen from above where the treatment section is raised in the surgical instrument of the first embodiment.
Figure 28:
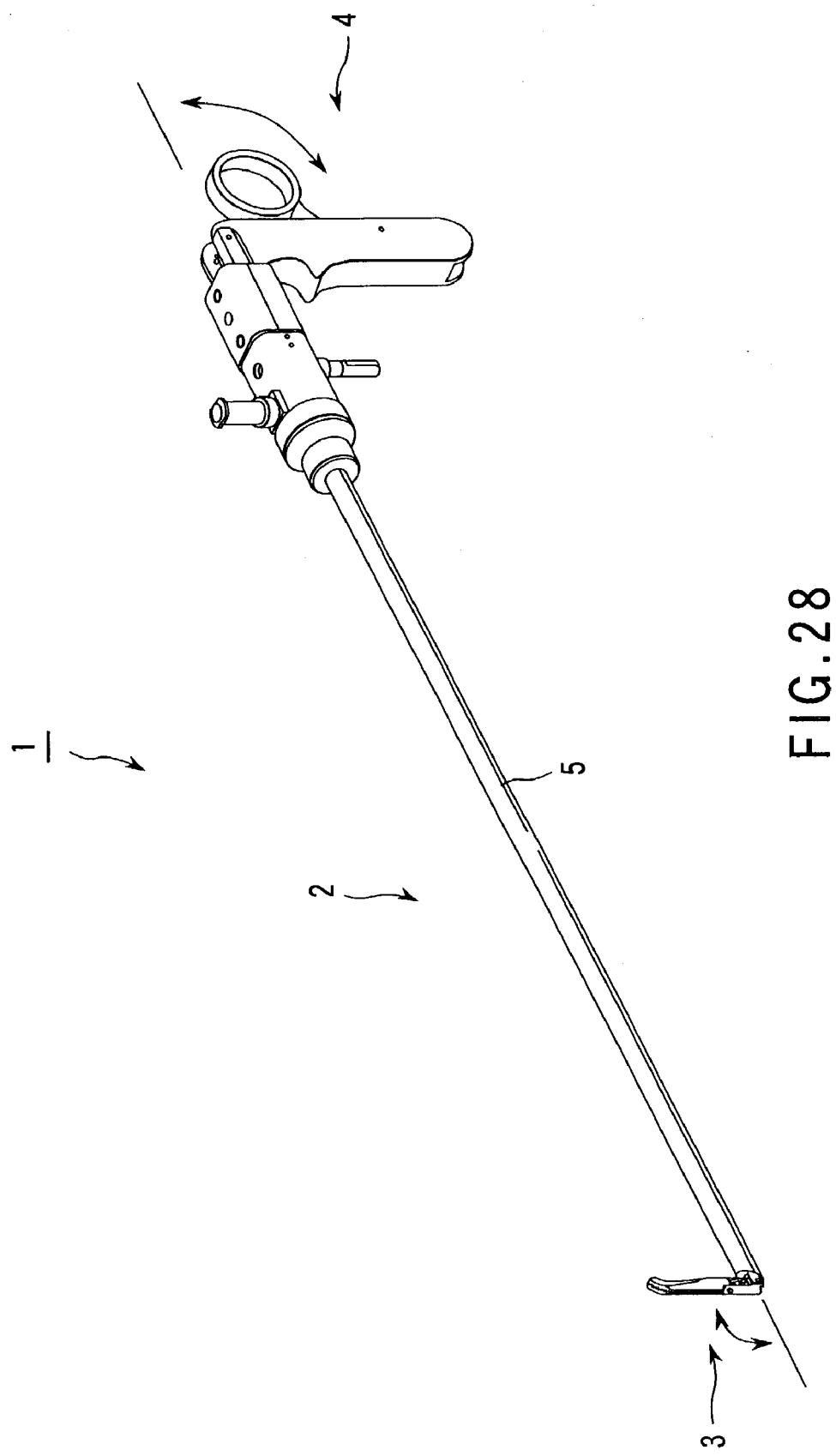
FIG. 28 is a perspective view of a state seen from above where the rotary handle of the operation section is rotated downward with respect to the insertion section to raise the treatment section with respect to the insertion section, showing the entire constitution of the surgical instrument of the first embodiment.
Figure 29:
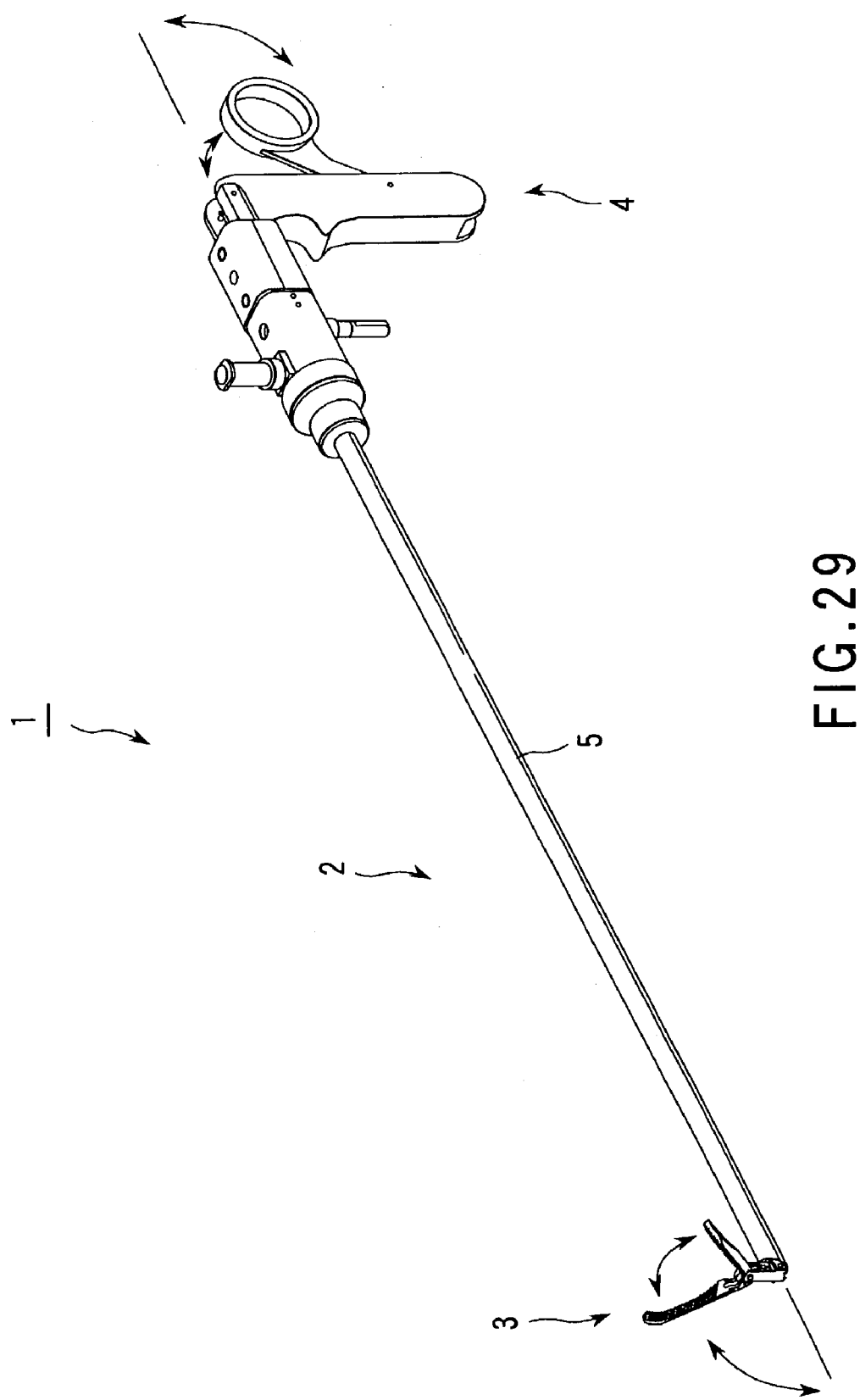
FIG. 29 is a perspective view of a state seen from above where the rotary handle of the operation section is rotated downward with respect to the insertion section, the opening/closing handle is opened with respect to the rotary handle, and the treatment section is raised with respect to the insertion section to open the jaw, showing the entire constitution of the surgical instrument of the first embodiment.

Then, the first and second jaws 101, 102 are rotated associatively with the rotation of the rotary cover 85. That is, when the rotary handle 32 is rotated downward around the second rotary pins 48a, 48b from the state of the surgical instrument 1 shown in FIG. 1, as shown in FIGS. 25 and 28, the treatment section 3 is raised from the proximal end of the rotary cover 85 to be rotated to a position of 90° with respect to the insertion section 2.

If the rotational amount of the rotary handle 32 with respect to the operation section main body 30 is 90° or lower, since the parallel states are maintained between the fourth rotary pin 83 and the third rotary pins 82a, 82b, and between the first connection pin 49 and the second rotary pins 48a, 48b, the treatment section 3 is rotated by an angle corresponding to the rotational amount of the rotary handle 32.

From this state, the opening/closing handle 42 is rotated with respect to the rotary handle 32 (see FIG. 19). From the state shown in FIG. 18 to the state shown in FIG. 19, the opening/closing handle 42 is rotated around the first rotary pin 43 in a direction to be opened with respect to the rotary handle 32.

The first connection members 51a, 51b of the rotary handle 32 are regulated in position. Thus, the second connection pin 55 of the proximal end of the opening/closing handle 42 is moved from the proximal end of the connection pin support 56 toward the distal end. The movement of the second connection pin 55 is accompanied by movements of the first connection members 51a, 51b toward the distal end of rotary handle 32. Upon the movements of the first connection members 51a, 51b to the distal end of the rotary handle 32, the second connection members 61a, 61b are moved toward the distal end of the rotary handle 32 by the third connection pin 64. At this time, since the position of the first driving rod 10 is regulated, the fourth connection pin 65 of the second connection members 61a, 61b is moved toward neither of the distal and proximal ends of the rotary handle 32. Then, the fourth connection pin 64 advances the first driving rod 10 to the front of the insertion section 2 while maintaining the same height.

As shown in FIGS. 14 and 15, the distal end of the first driving rod 10 advances along the center axis of the insertion section 2 to the treatment section 3 side. Upon the advancement of the first driving rod 10 along the center axis of the insertion section 2 to the treatment section 3 side, the third connection member 88 is advanced by the fifth connection pin 87 pivotally supported on the distal end of the first driving rod 10. Upon the advancement of the third connection member 88, the second abutment surface 94b of the third connection member 88 is moved while being abutted on the circular-arc proximal end surface of the fourth connection member 90. At this time, a direction of a normal force applied between the base end of the fourth connection member 90 and the second abutment surface 94b is brought gradually closer to the axial direction of the treatment section 3. Thus, the proximal end of the fourth connection member 90 is pushed up along the inside of the rotary cover 85 by the second abutment surface 94b. The fourth connection member 90 is advanced in the rotary cover 85 by the sixth connection pin 89. Upon the advancement of the fourth connection member 90, the seventh connection pin 96 advances in the rotary cover 85.

Figure 6:
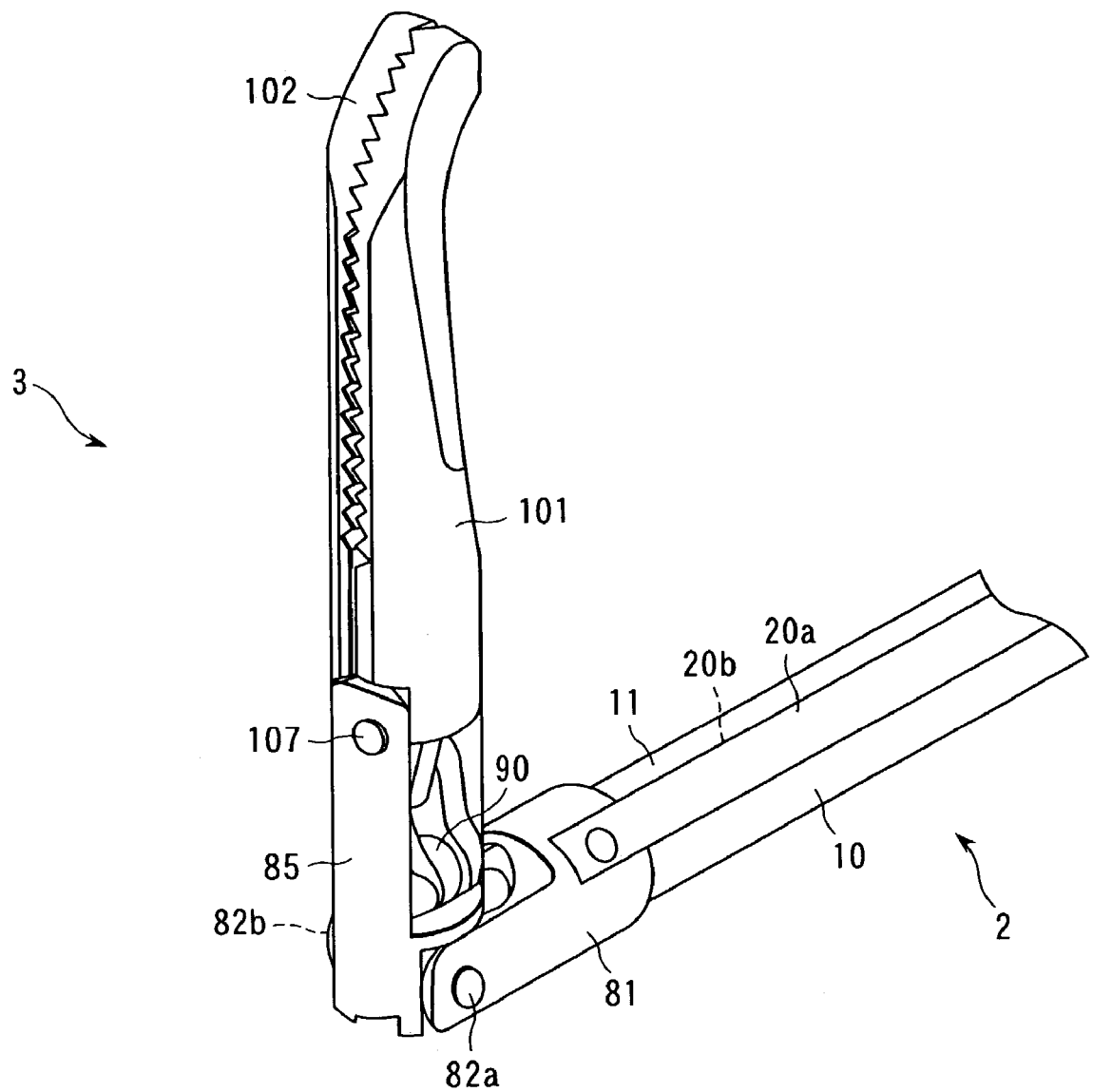
FIG. 6 is a perspective view of a state seen from above where the treatment section is raised while the sheath is removed from the insertion section in the surgical instrument of the first embodiment.
Figure 7:
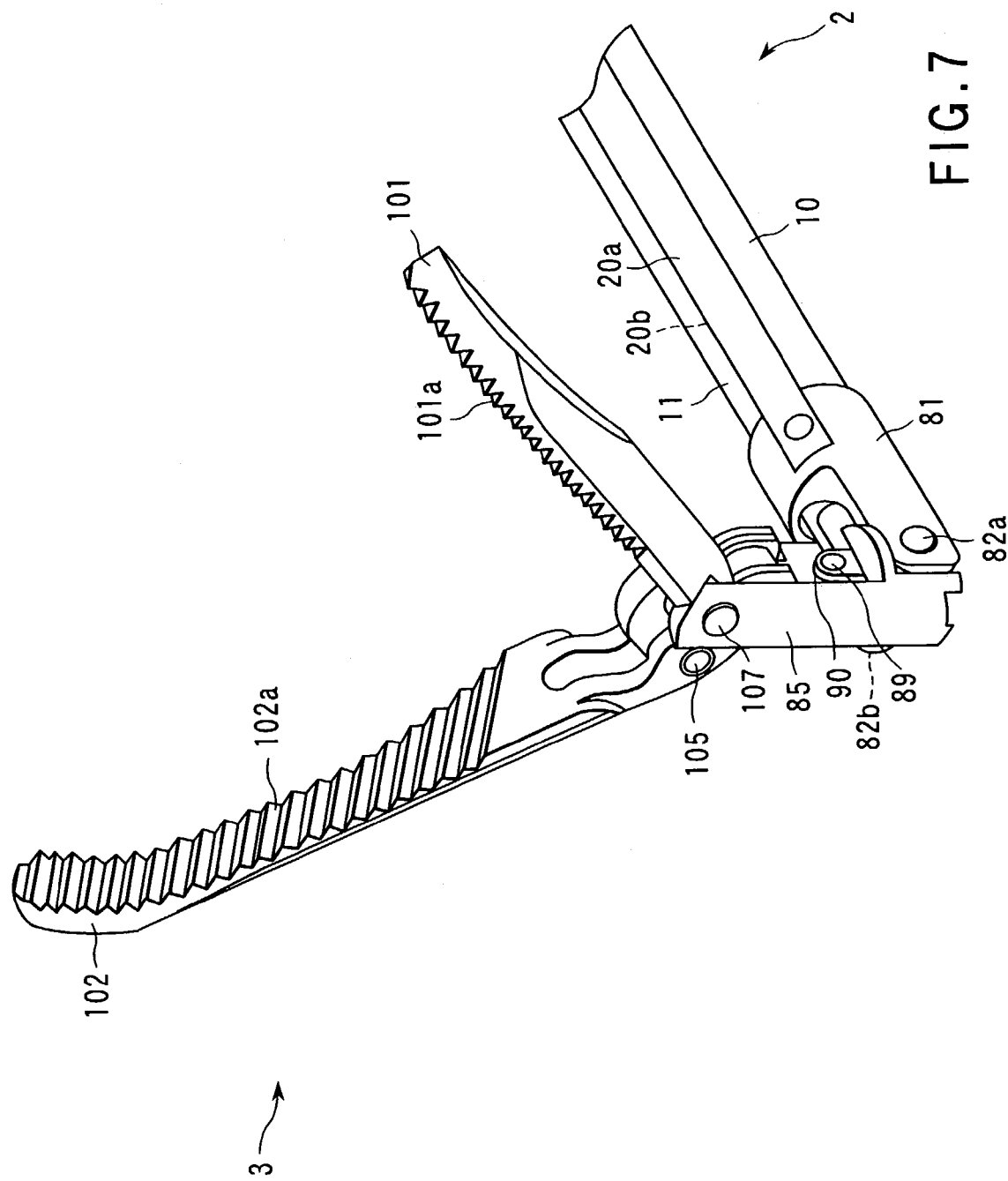
FIG. 7 is a perspective view of a state seen from above where the treatment section is raised and the jaw is opened while the sheath is removed from the insertion section in the surgical instrument of the first embodiment.
Figure 10:
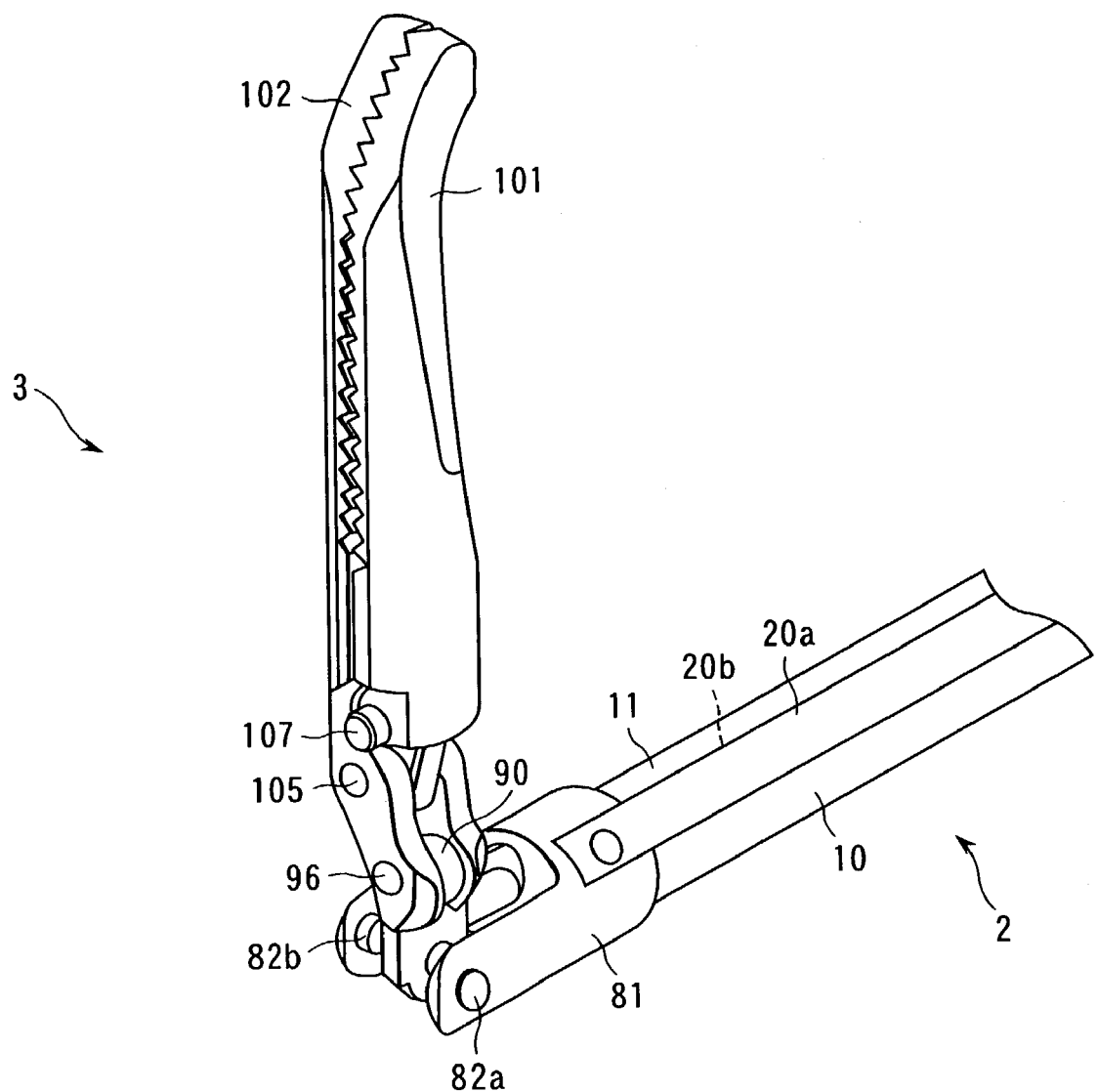
FIG. 10 is a perspective view of a state seen from above where the treatment section is raised while the sheath and the rotary cover are removed from the insertion section and the treatment section in the surgical instrument of the first embodiment.
Figure 11:
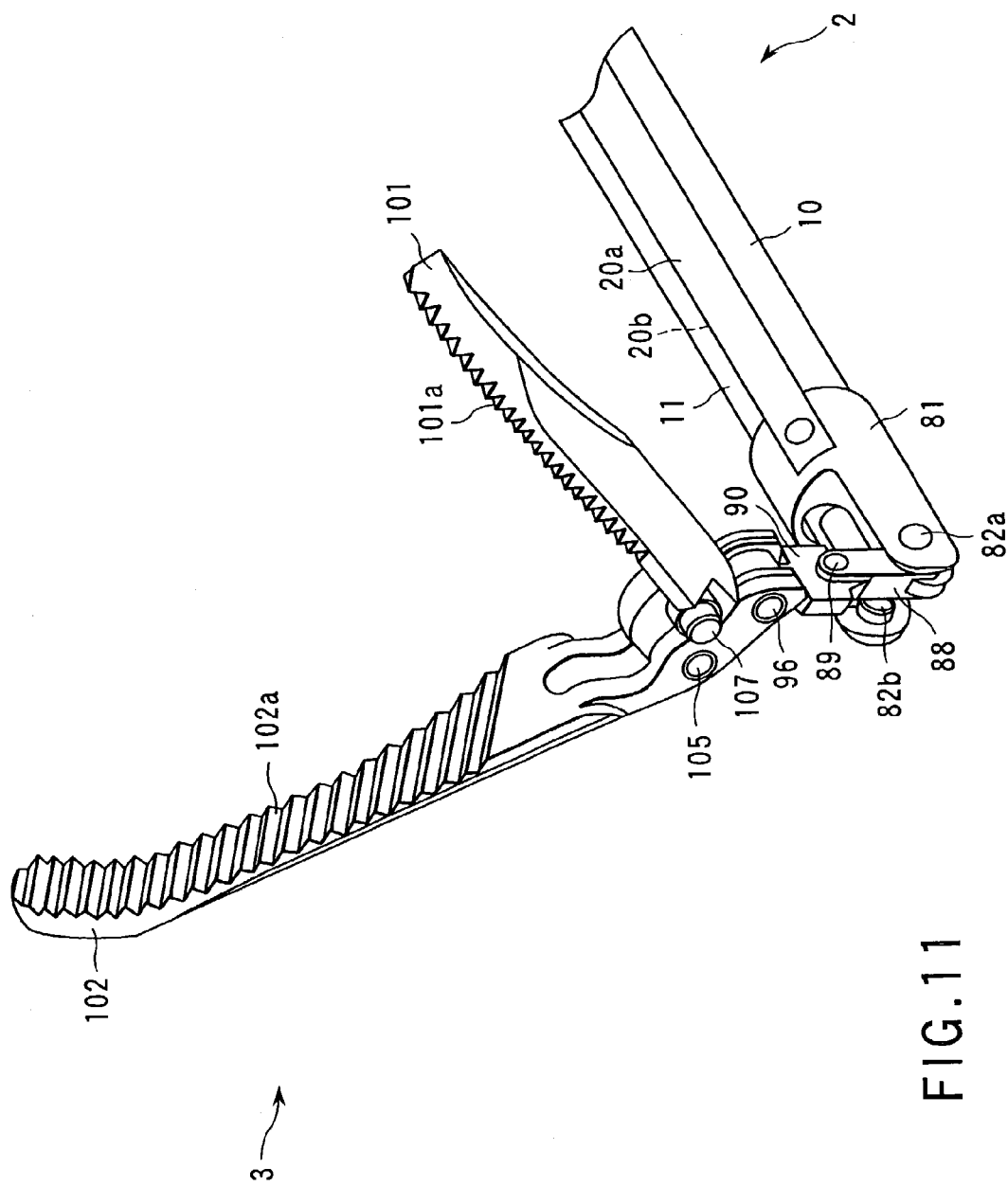
FIG. 11 is a perspective view of a state seen from above where the treatment section is raised and the jaw is opened while the sheath and the rotary cover are removed from the insertion section and the treatment section in the surgical instrument of the first embodiment.

As shown in FIGS. 6 and 7, for the first and second jaws 101, 102, the second opening/closing pin 107 is regulated in movement by the rotary cover 85. Accordingly, as shown in FIGS. 10 and 11, the first opening/closing pin 105 is moved to the side by using the seventh connection pin 96 as a supporting point. The movement of the first opening/closing pin 105 is accompanied by a movement of the second jaw 102 to the side by using the seventh connection pin 96 as a supporting point. Since the movement of the second opening/closing pin 107 is regulated, the first jaw 101 is opened with respect to the second jaw 102 associatively with the movement of the first opening/closing pin 105.

As shown in FIGS. 18 and 19, the second driving rod is not affected by the rotation of the opening/closing handle 42, and is unmoved.

Figure 26:
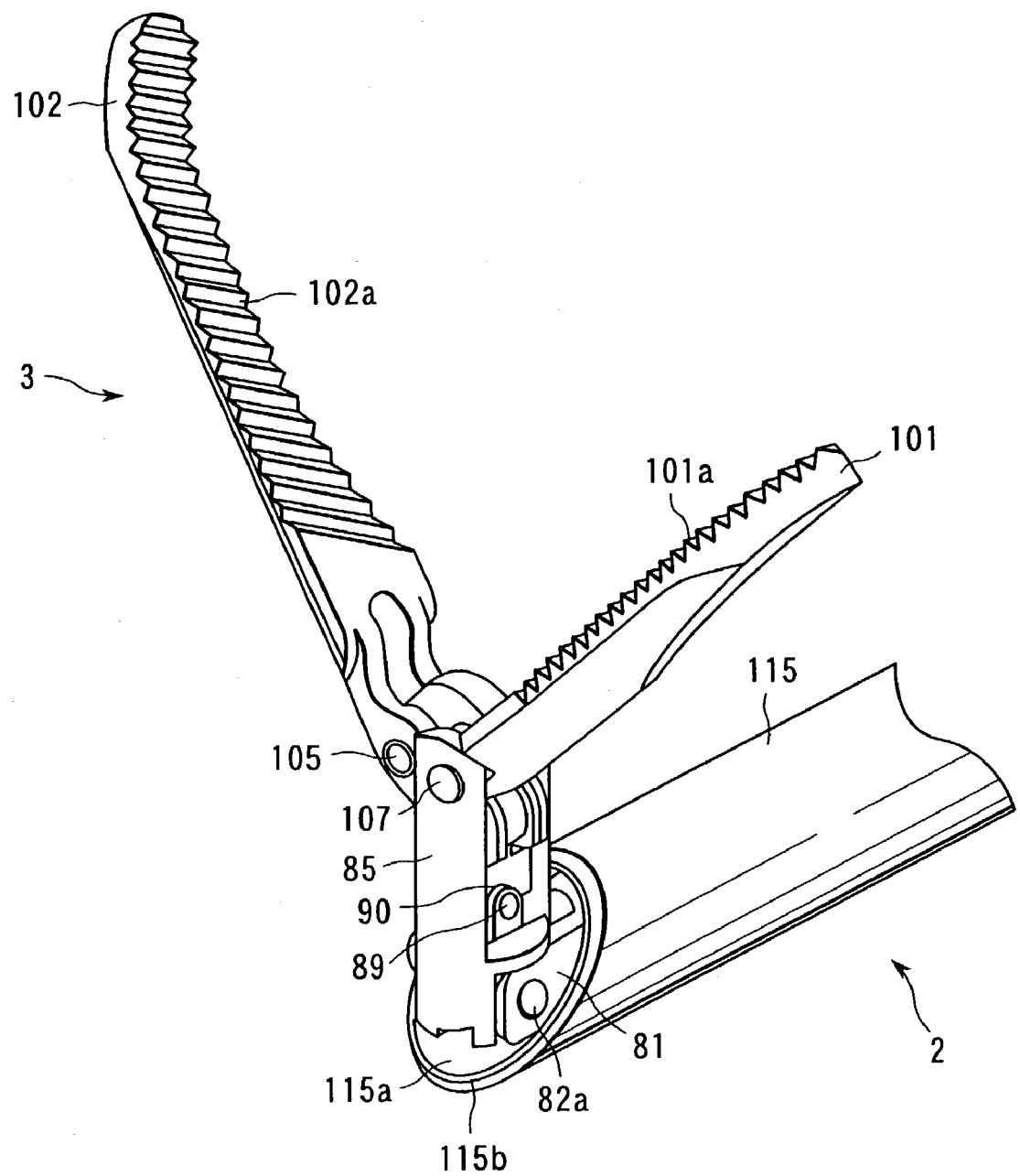
FIG. 26 is a perspective view of a state seen from above where the treatment section is raised and the jaw is opened in the surgical instrument of the first embodiment.

That is, when the opening/closing handle 42 is rotated upward around the first rotary pin 43 from the state of the surgical instrument 1 shown in FIG. 25, as shown in FIG. 26, the tip-tool of the treatment section 3 (first and second jaws 101, 102 relatively) is opened.

Thus, a proper treatment is carried out for the biomedical tissue by optionally combining the rotation of the rotary handle 32 with the rotation of the opening/closing handle 42. The shown rotational angle (e.g., 0° or 90°) and the opening angle of the treatment section 3 are not limited to the foregoing, but they can be set within a proper range, e.g., 45° between 0° and 90°.

This surgical instrument 1 is used, for example, when a tissue is dissected from a blood vessel stuck to the biomedical tissue. This treatment is carried out by, for example, opening the first and second jaws 101, 102 in a state where the treatment section 3 of the surgical instrument 1 is rotated by an optional angle with respect to the insertion section 2. At this time, the third connection member 88 maintains an abutted state on the distal end of the first driving rod 10 by the first abutment surface 94a (see FIG. 14). An abutted state on the proximal end of the fourth connection member 90 is maintained by the second abutment surface 94b. The first driving rod 10, the third connection member 88 and the fourth connection member 90 are made of rigid substances such as stainless materials. The opening/closing handle 42 is rotated to be separated from the rotary handle 32, thereby opening the first and second jaws 101, 102. The third connection member 88 is rotated in the axial direction of the rotary cover 85. The second abutment surface 94b of the third connection member 88 supports the fourth connection member 90 to move in a rotational direction. Thus, even in the rotated state of the treatment section 3 with respect to the insertion section 2, an opening force can be surely transmitted to the first and second jaws 101, 102 while maintaining the rotated state. Accordingly, the blood vessel stuck to the biomedical tissue can be easily dissected.

Additionally, a treatment of gripping the biomedical tissue may be carried out. Specifically, the treatment of picking the dissected blood vessel or gripping the biomedical tissue is carried out. The treatment is carried out by, for example, closing the first and second jaws 101, 102 in a state where the treatment section 3 of the surgical instrument 1 is rotated by an optional angle with respect to the insertion section 2. In this treatment, an operation reverse to that of dissecting the blood vessel from the biomedical tissue is carried out. The opening/closing handle 42 is rotated to approach the rotary handle 32, thereby closing the first and second jaws 101, 102. At this time, when the rotated state of the rotary handle 32 is maintained with respect to the operation section main body 30, the second driving rod 11 is unmoved with respect to the insertion section 2. Thus, only the first driving rod 10 is pulled to the proximal end side of the insertion section 2. Because of the abutments of the distal end of the first driving rod 10 on the proximal end of the third connection member 88 and the distal end of the third connection member 88 on the proximal end of the fourth connection member 90, the force applied to the first driving rod 10 can be surely transmitted to the fourth connection member 90 easily. Accordingly, the first and second jaws 101, 102 are closed to grip the biomedical tissue. The first driving rod 10, the third connection member 88 and the fourth connection member 90 are made of rigid substances such as stainless materials. Thus, even in the rotated state of the treatment section 3 with respect to the insertion section 2, a closing force can be surely transmitted to the first and second jaws 101, 102 while maintaining the rotated state. Then, the biomedical tissue and the blood vessel can be easily gripped.

A high-frequency treatment may be carried out for the biomedical tissue. The high-frequency input cord (not shown) is connected to the high-frequency input pin 73 of the operation section main body 30. When a high-frequency current (power) is supplied through the high-frequency input cord to the high-frequency input pin 73 to turn on electricity, the high-frequency current is transmitted from the tip-tool through the first driving rod 10, the third connection member 88 and the fourth connection member 90 to the biomedical tissue or the like. Accordingly, the high-frequency treatment is carried out for the biomedical tissue. At this time, insulation is secured from the distal end of the rotary handle 32 of the operation section 4 to the proximal end by a first insulating member 77 disposed in the vicinity of the proximal end of the first driving rod 10 and a second insulating member 78 disposed in the vicinity of the proximal end of the second driving rod 11. Additionally, the outer periphery of the third base 71 of the operation section main body 30 is covered with first and second covers 75a, 75b. The outer peripheral surface of the second base 67 of the operation section main body 30 is made of an insulating material. Thus, insulation is secured for the outer periphery of the operation section main body 30.

In the distal end of the insertion section 2, the extended portion 115a of the sheath 5 is disposed on the backside with respect to the rotational direction of the treatment section 3. Thus, when the high-frequency treatment is carried out in the rotated state of the treatment section 3, it is difficult for the vicinity of the proximal end of the rotary cover 85 to be brought into direct contact with biomedical tissue parts other than the target. Thus, execution of an unintended unnecessary high-frequency treatment on the biomedical tissue is prevented. As a result, operability is improved when the rotation of the treatment section 3 in a narrow space and the high-frequency treatment are simultaneously carried out.

There are other uses of the sheath 5. The sheath 5 may be used to dissect a tissue such as a blood vessel from the biomedical tissue or remove the biomedical tissue by using the extended portion 115a. Additionally, for example, the sheath 5 is rotated by 180° in the axial direction of the insertion section 2 to be attached. Then, it is possible to limit up-and-down rotation of the treatment section 3 of the instrument 1. That is, unexpected rotation of the treatment section 3 is prevented.

The insertion section 2 can be reinforced by disposing such a sheath 5 in the surgical instrument 1. Thus, even if the frames 20a, 20a are made thin or the like to reduce weight, the reduction in strength can be compensated for by fixing the sheath 5 to the insertion section 2.

As described above, the following can be said about the surgical instrument 1 of the embodiment.

In any rotational posture of the treatment section 3 between, e.g., 0° to 90° with respect to the insertion section 2, the treatment can be carried out while the tip-tool (first and second jaws 101, 102) has a sufficient opening/closing force and maintains an optional opening/closing angle. It is possible to prevent buckling of the treatment section 3 or rotation due to an unendurable force when the biomedical tissue is treated. Additionally, the high-frequency treatment can be carried out in such a state.

Since the first and second driving rods 10, 11 of the insertion section 2 are rigid, power can be efficiently transmitted by operating the rotary handle 32 and the opening/closing handle 42 of the operation section 4 quickly by one hand. Thus, the tip-tool of the treatment section 3 can be operated quickly. Even during the opening of the tip-tool, a sufficient rotational force can be transmitted.

Recessed and projected portions are formed on the grip surfaces 101a, 102a of the pair of jaws 101, 102. Accordingly, a suture needle, a suture thread, the biomedical tissue or the like to be gripped can be gripped securely.

In the distal end of the sheath insertion section 115 of the sheath 5, there is an area extended to the backside in the rotational direction of the treatment section 3. Accordingly, when the high-frequency treatment is carried out by the surgical instrument 1, it is possible to prevent an unnecessary high-frequency treatment for an unintended portion of the biomedical tissue. Thus, operability can be improved when the rotation of the treatment section 3 and the high-frequency treatment are simultaneously carried out in a narrow space. That is, the narrow space can be easily approached. When the sheath 5 is rotated by 180° in the axial direction of the insertion section 2 to be attached, the sheath 5 can function to prevent the up-and-down rotation of the treatment section 3 of the instrument 1. That is, unexpected rotation can be prevented.

By removing the sheath 5 from the insertion section 2 of the surgical instrument 1, after use of the surgical instrument 1, the inside of the insertion section 2 can be washed easily within a short time. When the first and second driving rods 10, 11, the frames 20a, 20b, and the regulation members 21a to 21c are exposed, these members can be directly washed by using a brush or the like. If the sheath 5 cannot be removed from the insertion section 2 such as during the operation, water (liquid) or air is sent into the insertion section 2 from the washing port 69 to enable easy washing.

According to the embodiment, only the second abutment surface 94b of the third connection member 88 is inclined. However, the first abutment surface 94a on which the distal end of the first driving rod 10 is abutted may also be inclined. Accordingly, a force applied from the first driving rod 10 can be surely transmitted to the fourth connection member 90 by the slope of the second abutment surface 94b of the third connection member 88.

The second connection members 61a, 61b arranged in the rotary handle 32 of the operation section 4 may comprise third and fourth abutment surfaces as in the case of the third connection member 88. Accordingly, a force applied from the opening/closing handle 42 can be surely transmitted from the first connection members 51a, 51b to the first driving rod 10 by the third and fourth abutment surfaces of the second transmission members 61a, 61b. The first and second jaws 101, 102 are not limited to those shown in the drawings. For example, they may be formed in a shape of scissors, dissecting forceps or the like.

If the high-frequency treatment is not carried out, the first driving rod 10, the third connection member 88, the fourth connection member 90 and the tip-tool need not be conductive. That is, these members need not be limited to stainless materials. For example, rigid members which enable various surgical treatments for the biomedical tissue may be used, as long as they can dissect the blood vessel of the biomedical tissue, and maintain a closed state even if the biomedical tissue is pulled while the tip-tool is closed and the biomedical tissue is gripped. For example, reinforced plastic may be used for the first driving rod 10, the third connection member 88, the fourth connection member 90 and the tip-tool.

Each of the pair of jaws 101, 102 is a type of end effecter (the tip-tool), and the jaw is not limited to this. The end effecter can be used as a type to open/close only one of the pair of jaws 101, 102 to the other, as a heat probe to generate heat in one of the pair of jaws 101, 102, or the like.

Figure 30:
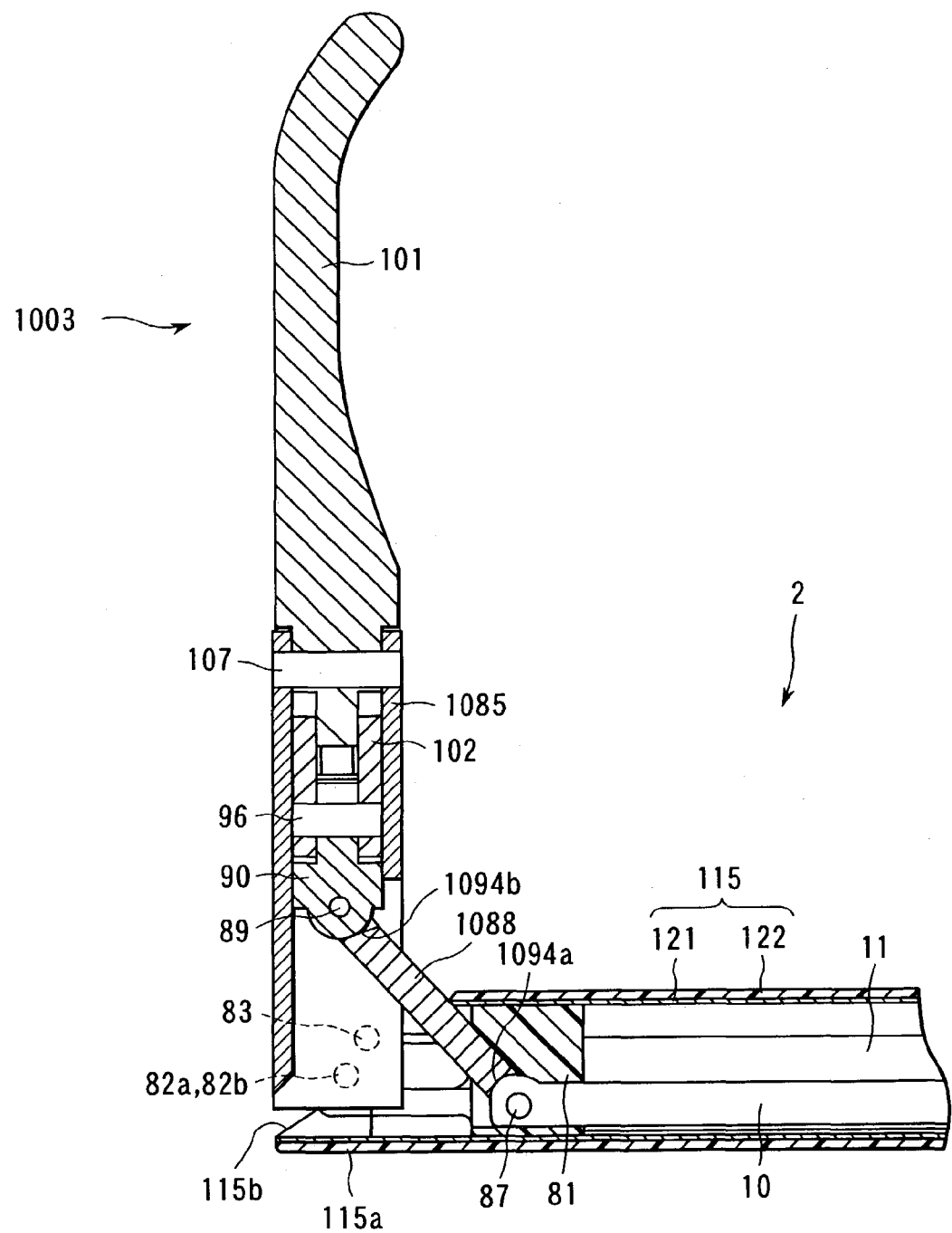
FIG. 30 is a sectional view along the line B-B of FIG. 2 showing a state where a treatment section is raised with respect to an insertion section in a surgical instrument according to a second embodiment.

A second embodiment will be described with reference to FIGS. 30 and 31. This embodiment is a modified example of the first embodiment, members of similar constitutions, functions, operations etc., are denoted by similar reference numerals, and detailed description will be omitted.

A treatment section 100 of a surgical instrument 1 of the embodiment will be described by referring to FIG. 30. A rigid fourth base 81 is disposed on the distal end side of the insertion section 2 to project forward. Tips of not-shown frameworks 20a, 20b are fixed to a proximal end of the fourth base 81. A rotary cover 1085 is connected to the distal end of the fourth base 81, which can be rotated up and down by third rotary pins 82a, 82b arranged orthogonally to an axial direction of the insertion section 2. The rotary cover 1085 is rotatably connected to a distal end of a second driving rod 11 by a fourth rotary pin 83 parallel to the third rotary pins 82a, 82b.

A proximal end of a third connection member 1088 is connected to a distal end of a first driving rod 10 by a fifth connection pin 87. A proximal end of a fourth connection member 90 is connected to a distal end of the third connection member 1088 by a sixth connection pin 89. The fourth connection member 90 is interpolated to slide in the rotary cover 1085.

In the rotary covert 1085, a second opening/closing pin 107 is disposed in a direction orthogonal to the third rotary pins 82a, 82b. A first jaw 101 is rotatably connected to the second opening/connecting pin 107. A second jaw 102 is rotatably connected to a proximal end of the first jaw 101 by a first opening/closing pin 105. The first and second jaws 101, 102 are mutually rotated by using the first opening/closing pin 105 as a supporting point.

The third connection member 1088 is abutted on the distal end of the first driving rod 10 by a first abutment surface 1094a. It is abutted on a circular-arc proximal end of the fourth connection member 90 by a second abutment surface 94b. A second abutment surface 1094b is inclined in a normal direction orthogonal to an axial direction of the third connection member 1088. Accordingly, it is possible to reduce resistance when the third connection member 1088 pushes up the fourth connection member 90. For this third connection member 1088, a distance between the first and second abutment surfaces 1094a, 1094b is longer than that for the third connection member 88 of the first embodiment. Thus, a direction of a normal force on the second abutment surface 1094a can be brought closer to an axial direction of the treatment section 3.

For example, inclination angles of the second abutment surfaces 94b, 1094b of the third connection members 88, 1088 of the first embodiment and the present embodiment are set equal. An angle of a surface of pushing up the rotary cover 1085 is brought closer to the axial direction of the treatment section 3 for the second abutment surface 1094b of the third connection member 1088 of the present embodiment than for the second abutment surface 94b of the third connection member 88 of the first embodiment. Accordingly, when equal forces are applied to the third connection members 88, 1088, component forces applied from the second abutment surfaces 94b, 1094b to the fourth connection members 90 can be enlarged.

An operation section 1004 will now be described by referring to FIG. 31. Ends of second connection members 1061a, 1061b are connected to distal ends of first connection members 51a, 51b by a third connection pin 64. The other ends of the second connection members 1061a, 1061b are connected to the proximal end of the first driving rod 10. The second connection members 1061a, 1061b are formed longer than the second connection members 61a, 61b of the first embodiment. The second connection members 1061a, 1061b are disposed to be parallel to the third connection member 1088.

Description will be made of an operation of the surgical instrument 1 of the embodiment.

Figure 31:
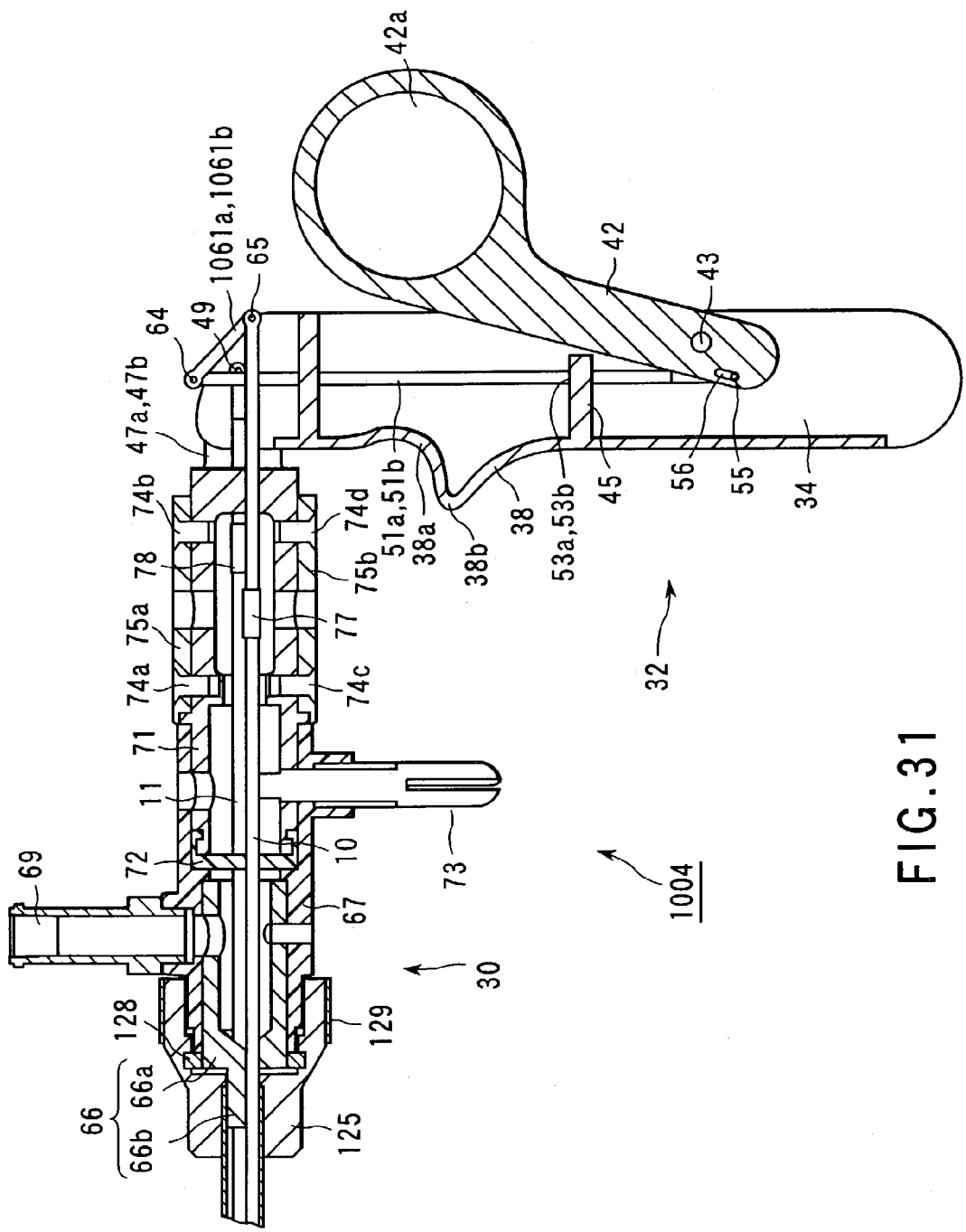
FIG. 31 is a sectional view along the line B-B of FIG. 2 showing a state where a rotary handle of an operation section is lowered with respect to an operation section main body in the surgical instrument of the second embodiment.

An opening/closing handle 42 shown in FIG. 31 is rotated with respect to a rotary handle 32 by using a first rotary pin 43 as a center (supporting point). The first connection members 51a, 51b move back and forth in parallel with a longitudinal direction axis of the rotary handle 32. The back and forth movements of the first connection members 51a, 51b are accompanied by associative movements of third connection members 1041a, 1041b. The movements of the third connection members 1041a, 1041b are accompanied by a back and forth movement of the first driving rod 10. Further, by the back and forth movement of the first driving rod 10, the third connection member 1088 shown in FIG. 30 is moved back and forth.

In this case, an angle between a center axis direction of the third connection member 1088 and a center axis direction of the treatment section 1003 is sharper than that between the center axis direction of the third connection member 88 and the center axis direction of the treatment section 3. Thus, the resistance is reduced more than that in the constitution of the first embodiment to enable a back and forth movement of the fourth connection member 90.

From the foregoing description, the following can be said about the surgical instrument 1 of the embodiment. In any rotational posture of the treatment section 1003 between 0° and 90° with respect to the insertion section 2, the rotational posture can be maintained when the operation section 1004 is operated. In this case, when the opening/closing handle 42 is operated with respect to the rotary handle 32, a direction of a normal force applied between the second abutment surface 1094b and the base end of the fourth connection member 90 can be brought close to the axial direction of the treatment section 1003. Thus, the third connection member 1088 can open/close the tip-tool (first and second jaws 101, 102) by an optional opening/closing angle in a state where the tip-tool has a sufficient opening/closing force.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A surgical instrument comprising:
    an insertion section having a distal end portion and a proximal end portion, the insertion section comprising first and second driving rods which are disposed side by side and each of which has a distal end portion and a proximal end portion;
    a pair of jaws disposed in the distal end portion of the insertion section;
    a support which pivotally supports at least one jaw of the pair of jaws to be relatively opened/closed;
    a sliding member which supports the at least one jaw of the pair of jaws being pivotally supported by the support, and which is slid in an axial direction of the support with respect to the support to relatively open/close the at least one jaw of the pair of jaws being pivotally supported by the support;
    a connecting rod having a distal end portion and a proximal end portion, the sliding member being pivotally supported on the distal end portion of the connecting rod to open/close the pair of jaws, and the distal end portion of the first driving rod being pivotally supported on the proximal end portion of the connecting rod;
    a rotation mechanism which rotatably supports the support on the distal end portion of the insertion section, and pivotally supports the support on the distal end portion of the second driving rod in a state of being offset with respect to a center axis of the support; and
    an operation section disposed in the proximal end portion of the insertion section, which pivotally supports the proximal end portions of the first and second driving rods when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support on the distal end portion of the insertion section, thereby rotating the pair of jaws relatively with respect to the insertion section,
    wherein the connecting rod has rigidity which opens/closes the pair of jaws for a biomedical tissue in a state where a rotational position of the pair of jaws with respect to the insertion section has been held to enable treatment of the biomedical tissue, and wherein the connecting rod is made of a metal material, and
    wherein the first driving rod is arranged in a position of being offset with respect to a center axis of the insertion section,
    the sliding member is arranged on a center axis of the support, and when the insertion section and the support are arranged on the same axis, an axial direction of the connecting rod is inclined in an axial direction of the insertion section and the support, and, wherein the sliding member has a circular-arc surface, and a distal end portion of the connecting rod has an abutment surface abutted on the circular-arc surface of the sliding member.

2. The surgical instrument according to claim 1, wherein the abutment surface of the connecting rod has inclination in the axial direction of the connecting rod.

3. The surgical instrument according to claim 2, wherein the pair of jaws have treatment section opening/closing mechanisms which are opened oppositely to each other in the axial direction of the support.

4. The surgical instrument according to claim 3, wherein the treatment section opening/closing mechanisms comprise:
a first connection pin which supports a proximal end portion of one jaw of the pair of jaws at the distal end portion of the sliding member,
a second connection pin which supports another jaw of the pair of jaws to be opened/closed with respect to the one jaw of the pair of jaws, and
a regulation member which regulates a movement of the support.

5. A surgical instrument comprising:
an insertion section having a distal end portion and a proximal end portion, the insertion section comprising a first driving rod and a second driving rod disposed side by side, each of the first driving rod and the second driving rod having a distal end portion and a proximal end portion;
a pair of jaws disposed in the distal end portion of the insertion section;
a support positioned to pivotally support at least one jaw of the pair of jaws to be opened/closed relative to the pair of jaws;
a sliding member supporting the at least one jaw of the pair of jaws and to slide in an axial direction of the support with respect to the support to relatively open/close the at least one jaw;
a connecting rod having a distal end portion and a proximal end portion, the sliding member being pivotally supported on the distal end portion of the connecting rod to open/close the pair of jaws, and the distal end portion of the first driving rod being pivotally supported on the proximal end portion of the connecting rod, the sliding member being supported at the distal end portion of the connecting rod such that the sliding member is pushed to slide in a distal direction to open the pair of jaws;
a rotation mechanism rotatably supporting the support on the distal end portion of the insertion section, and pivotally supporting the support on the distal end portion of the second driving rod in a state of being offset with respect to a center axis of the support; and
an operation section disposed in the proximal end portion of the insertion section, and pivotally supporting the proximal end portions of the first and second driving rods when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support on the distal end portion of the insertion section, thereby rotating the pair of jaws relatively with respect to the insertion section, wherein the connecting rod has rigidity which opens/closes the pair of jaws for a biomedical tissue in a state where a rotational position of the pair of jaws with respect to the insertion section has been held to enable treatment of the biomedical tissue, wherein the first driving rod is arranged in a position of being offset with respect to a center axis of the insertion section, the sliding member is arranged on a center axis of the support; and when the insertion section and the support are arranged on the same axis, an end surface in an axial direction of the connecting rod is inclined in an axial direction of the insertion section and the support;

wherein the sliding member has a circular-arc surface, and a distal end portion of the connecting rod has an abutment surface abutted on the circular-arc surface of the sliding member.

6. The surgical instrument according to claim 5, wherein the abutment surface of the connecting rod has inclination in the axial direction of the connecting rod.

7. The surgical instrument according to claim 6, wherein the pair of jaws have treatment section opening/closing mechanisms which are opened oppositely to each other in the axial direction of the support.

8. The surgical instrument according to claim 7, wherein the treatment section opening/closing mechanisms comprise:
a first connection pin which supports a proximal end portion of one jaw of the pair of jaws at the distal end portion of the sliding member;
a second connection pin which supports another jaw of the pair of jaws to be opened/closed with respect to the one jaw of the pair of jaws; and
a regulation member which regulates a movement of the support.

9. A surgical instrument comprising:
an insertion section having a distal end portion and a proximal end portion, the insertion section comprising first and second driving rods which are disposed side by side and each of which has a distal end portion and a proximal end portion;
a pair of jaws disposed in the distal end portion of the insertion section;
a support which pivotally supports at least one jaw of the pair of jaws to be relatively opened/closed;
a sliding member which supports the at least one jaw of the pair of jaws being pivotally supported by the support, and which is slid in an axial direction of the support with respect to the support to relatively open/close the at least one jaw of the pair of jaws being pivotally supported by the support;
a connecting rod having a distal end portion and a proximal end portion, the sliding member being pivotally supported on the distal end portion of the connecting rod to open/close the pair of jaws, and the distal end portion of the first driving rod being pivotally supported on the proximal end portion of the connecting rod;
a rotation mechanism which rotatably supports the support on the distal end portion of the insertion section, and pivotally supports the support on the distal end portion of the second driving rod in a state of being offset with respect to a center axis of the support;

an operation section disposed in the proximal end portion of the insertion section, which pivotally supports the proximal end portions of the first and second driving rods when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support on the distal end portion of the insertion section, thereby rotating the pair of jaws relatively with respect to the insertion section, wherein the operation section has an operation section main body which comprises a distal end portion and a proximal end portion, through which the first and second driving rods are inserted, the distal end portion of the operation section main body being connected to the proximal end portion of the insertion section, a rotary handle which has a distal end portion and a proximal end portion, the distal end portion of the rotary handle being rotated in one plane with respect to the proximal end portion of the operation section main body;

an opening/closing handle supported to be opened/closed with respect to the rotary handle;

wherein the distal end portion of the rotary handle is pivotally supported on the proximal end portion of the second driving rod so that when the rotary handle is rotated in one plane in an axis of the operation section main body, the second driving rod moves back and forth in the axial direction of the second driving rod, wherein the rotary handle has a first operation section connecting rod which has a distal end portion and a proximal end portion, the proximal end portion of the first operation section connecting rod being supported by the opening/closing handle so that the first operation section connecting rod moves back and forth associatively with opening/closing of the opening/closing handle with respect to the rotary handle by a pivotal support which pivotally supports the opening/closing handle, a second operation section connecting rod which has one end portion and another end portion, the one end portion of the second operation section connecting rod being connected to the distal end portion of the first operation section connecting rod, and the other end portion being connected to the proximal end portion of the first driving rod, wherein the rotary handle comprises a first grip which holds a finger other than a thumb, and the opening/closing handle comprises a second grip which is pivotally supported by a pivotal support disposed not in a position where the thumb is arranged but on the proximal end portion of the rotary handle, and which holds the thumb not on the pivotal support but on the distal end portion side of the rotary handle.

10. A surgical instrument comprising:

first and second driving rods which are disposed side by side and each of which has distal and proximal end portions;

an operation section disposed in the proximal end portions of the first and the second driving rods, opened/closed and rotated to transmit an opening/closing force to the first driving rod, and a rotating force to the second driving rod; and a treatment section disposed in the distal end portions of the first and second driving rods, the treatment section comprising:

a pair of jaws to be relatively opened/closed;

a support which supports at least one jaw of the pair of jaws, and pivotally supports the distal end portion of the second driving rod to move in one plane in an axis of the second driving rod;

a sliding member which is supported by the at least one jaw of the pair of jaws, and which is slid in an axial direction of the support to relatively open/close the pair of jaws; and connection means having rigidity which connects the distal end portion of the first driving rod to the sliding member to hold a rotational state and an opened/closed state of the pair of jaws, the sliding member being supported at the distal end portion of the connection means such that the sliding member is pushed to slide in a distal direction to open the pair of jaws, wherein the distal end portion of the first driving rod comprises a circular-arc surface, and the connection means comprises a rod member which has a distal end portion connected to the sliding member and a proximal end portion connected to the distal end portion of the first driving rod, the proximal end portion of the rod member having an abutment surface abutted on the distal end portion of the first driving rod having the circular-arc surface to regulate a rotational direction of the support.

11. The surgical instrument according to claim 10, wherein the abutment surface of the rod member is inclined in an axial direction of the rod member.

12. The surgical instrument according to claim 10, wherein the sliding member comprises a circular-arc surface, and the connection means comprises a rod member which has a distal end portion connected to the sliding member and a proximal end portion connected to the distal end portion of the first driving rod, the distal end portion of the rod member having an abutment surface abutted on the circular-arc surface of the sliding member to regulate a rotational direction of the support.

13. The surgical instrument according to claim 12, wherein the abutment surface of the rod member is inclined in an axial direction of the rod member.

14. A surgical instrument comprising:

an insertion section having a distal end portion and a proximal end portion, the insertion section including a first driving rod and a second driving rod disposed side by side and each of the first driving rod and the second driving rod having a distal end portion and a proximal end portion;

a pair of jaws disposed in the distal end portion of the insertion section;

a support positioned to pivotally support at least one jaw of the pair of jaws to be opened/closed relative to the pair of jaws;

a sliding member positioned to support the at least one jaw and to slide in an axial direction of the support with respect to the support to relatively open/close the at least one jaw;

a connecting rod having a distal end portion and a proximal end portion, the sliding member being pivotally supported on the distal end portion of the connecting rod to open/close the pair of jaws, and the distal end portion of the first driving rod being pivotally supported on the proximal end portion of the connecting rod;

a rotation mechanism rotatably supporting the support on the distal end portion of the insertion section, and pivotally supporting the support on the distal end portion of the second driving rod in a state of being offset with respect to a center axis of the support; and an operation section disposed in the proximal end portion of the insertion section, and pivotally supporting the proximal end portions of the first and second driving rods when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support on the distal end portion of the insertion section, thereby rotating the pair of jaws relatively with respect to the insertion section, wherein the sliding member has a circular-arc surface, and a distal end portion of the connecting rod has an abutment surface abutted on the circular arc surface of the sliding member, wherein the abutment surface of the connecting rod is inclined in the axial direction of the connecting rod.

15. A surgical instrument comprising:

an insertion section having a distal end portion and a proximal end portion, the insertion section comprising a first driving rod and a second driving rod disposed side by side and each of which has a distal end portion and a proximal end portion;

a pair of jaws disposed in the distal end portion of the insertion section;

a support positioned to pivotally support at least one jaw of the pair of jaws to be opened/closed relative to the pair of jaws;

a sliding member which supports the at least one jaw of the pair of jaws and to slide in an axial direction of the support with respect to the support to relatively open/close the at least one jaw;

a connecting rod having a distal end portion and a proximal end portion, the sliding member being pivotally supported on the distal end portion of the connecting rod to open/close the pair of jaws, and the distal end portion of the first driving rod being pivotally supported on the proximal end portion of the connecting rod, the sliding member being supported at the distal end portion of the connecting rod such that the sliding member is pushed to slide in a distal direction to open the pair of jaws;

a rotation mechanism which rotatably supports the support on the distal end portion of the insertion section, and pivotally supports the support on the distal end portion of the second driving rod in a state of being offset with respect to a center axis of the support; and an operation section disposed in the proximal end portion of the insertion section, and pivotally supporting the proximal end portions of the first and second driving rods when the operation section is opened/closed and rotated, an opening/closing force by the opening/closing operation being transmitted from the proximal end portion to the distal end portion of the first driving rod to slide the sliding member on the support through the connecting rod thereby opening/closing the pair of jaws, and a rotating force by the rotation operation being transmitted from the proximal end portion to the distal end portion of the second driving rod to apply a rotational force on the support to rotate the support on the distal end portion of the insertion section, thereby rotating the pair of jaws relatively with respect to the insertion section, wherein the pair of jaws have treatment section opening/closing mechanisms which are opened oppositely to each other in the axial direction of the support, wherein the treatment section opening/closing mechanisms comprise:

a first connection pin which supports a proximal end portion of one jaw of the pair of jaws at the distal end portion of the sliding member;

a second connection pin which supports another jaw of the pair of jaws to be opened/closed with respect to the one jaw of the pair of jaws; and a regulation member which regulates a movement of the support and the first connection pin, wherein when the insertion section and the support are arranged on the same axis, an end surface in an axial direction of the connecting rod is inclined in an axial direction of the insertion section and the support.

* * * * *